United States Patent
La Rosa et al.

(10) Patent No.: US 7,489,012 B2
(45) Date of Patent: Feb. 10, 2009

(54) DEVICE FOR CONFINING LIVE NEURAL CELLS CULTIVATED ON A CHIP OF NONINVASIVE NEUROELECTRONIC INTERFACING

(75) Inventors: Manuela La Rosa, Giarre (IT); Donata Nicolosi, San Gregorio (IT); Luigi Occhipinti, Ragusa (IT); Giuseppe Spoto, Mascalucia (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 655 days.

(21) Appl. No.: 11/040,080

(22) Filed: Jan. 21, 2005

(65) Prior Publication Data

US 2005/0288713 A1    Dec. 29, 2005

(30) Foreign Application Priority Data

Jan. 23, 2004    (IT)    ............ VA2002A0003

(51) Int. Cl.
*H01L 29/00* (2006.01)
*C12M 1/34* (2006.01)

(52) U.S. Cl. ............. 257/414; 257/E29.112; 435/305.3; 607/115

(58) Field of Classification Search ............. 257/414, 257/E29.112; 435/305.3; 607/115
See application file for complete search history.

(56) References Cited

U.S. PATENT DOCUMENTS 6,416,170 B2 * 7/2002 Silverbrook ............ 347/54
6,667,172 B2 * 12/2003 Janigro et al. ............ 435/297.4
6,691,513 B1 * 2/2004 Kolesar ............ 60/527
6,775,048 B1 * 8/2004 Starkweather et al. ...... 359/291

OTHER PUBLICATIONS

M. Maher, "The Neurochip: a new multielectrode device for stimulating and recording from cultured neurons," J. of Neuroscience Methods, vol. 87, 1999, p. 45-56.*

Wright et al., Towards a Functional MEMS Neurowell by Physiological Experimentation, Technical Digest: ASME 1996 International Mechanical Engineering Congress and Exposition, DSC-vol. 59, Atlanta, GA, pp. 333-338, Nov. 1996.

Zeck et al., Noninvasive neuroelectronic interfacing with synaptically connected snail neurons immobilized on a semiconductor chip, Proc Natl Acad Sci USA 98(18):10457-62, Aug. 2001.

Maher et al., The neurochip: A new multielectrode device for stimulating and recording from cultured neurons, J. Neurosci. Meth. 87:45-56, 1999.

* cited by examiner

*Primary Examiner*—Douglas M Menz
*Assistant Examiner*—Steven J. Fulk
(74) *Attorney, Agent, or Firm*—Baker & McKenzie LLP

(57) ABSTRACT

The invention is directed to a microdevice for containing electrically coupled cells while allowing their growth that allows the addition or removal of cells from their containment by providing an actuatable gate. When the gate is actuated, for example with electric current, the cells may be added or removed from their containment. The invention may be applied to a neurochip or any device for growing cells in a defined spatial arrangement.

21 Claims, 25 Drawing Sheets

DEVICE FOR CONFINING LIVE NEURAL CELLS CULTIVATED ON A CHIP OF NONINVASIVE NEUROELECTRONIC INTERFACING

CROSS-REFERENCE TO RELATED APPLICATIONS

This application claims priority to Italian Application No. VA2004A000003 filed Jan. 23, 2004, incorporated in its entirety by reference.

STATEMENT REGARDING FEDERALLY SPONSORED RESEARCH OR DEVELOPMENT

Not applicable.

REFERENCE TO A COMPACT DISK APPENDIX

Not applicable.

FIELD OF THE INVENTION

This invention relates in general to microelectronic devices for studying biological phenomena at, a cellular level and more precisely to a method and a device for confining cells, for example neural cells, on a chip of noninvasive neuroelectronic interfacing.

BACKGROUND OF THE INVENTION

Individual neurons from different parts of the brain may be taken from animals and cultivated in biologically compatible environments. However, if an ex vivo neural network could be established, it could then be studied by stimulating neurons with electric signals and observing how the live network reacts and modifies itself. This could bring us closer to understanding how a neural network modifies its structure during the learning phase and the rules that govern the way synapses and neurites grow. The analysis of the electro-physiological activity of the neurons in the neural network may allow us to develop artificial prostheses for by-passing injured zones and restore brain functionality, or to realize neuro-diagnostic tools for monitoring the reaction of biological neurons to selected chemical species or newly developed drugs. But in order to reach this objective, we need suitable devices for maintaining a live neural network with electrical stimulation and detection capabilities.

Specifically, we need a device that can spatially arrange a plurality of live neurons at individual fixed positions with reliable and durable electrical coupling to stimulation and detection circuitry. The device should allow the confined neurons to grow and develop synaptic connections for creating a neural network and communication. For applying and detecting electric signals there must be means for ensuring a stable contact of the body of each spatially confined neuron to an electrode or with a functionally equivalent electrical coupling element, connected to a circuit for stimulating neurons and for detecting electrical signals exchanged among them.

There are many research teams that study neural activity by stimulating and recording electrical signals coming from distinct zones of a nervous tissue (hippocampus, cortex etc.), but the main difficulty is electrically coupling external stimulation and sensing circuitries to the neurons.

This is currently established through coupling elements of two kinds: invasive interfaces (electrodes are implanted "in vivo" in a nervous tissue); and noninvasive interfaces (where neural tissue contacts a silicon chip substrate establishing an electrical coupling with an embedded electrode).

The main drawback of invasive interfaces, typically employing intra-cellular electrodes, is the risk of irremediably damaging the cell during experiments. Moreover, it is very difficult to use more than two electrodes at the same time for stimulating the neural network because the actuators used for correctly positioning the microelectrodes are very cumbersome.

In order to overcome this problem, effective noninvasive interfaces for coupling neurons to external electronic devices are being earnestly searched and developed. For example, Dr. Roberta Diaz Brinton grew rat hippocampus neurons on a silicon substrate at the University of Southern California. The objective of his experiment was to use hybrid brain-silicon systems for studying the processes by which a brain carries out complex operations, such as pattern recognition.

According to this methodology, dissociated neurons were placed on a silicon test substrate having an array of electrodes and coated with a material to which the neural cells could stably adhere. The neurons fixed themselves to the silicon substrate and grew, sprouting processes and synaptic connections with other neurons. The growth of the neurons colonies was directable: by using masks, it was possible to predefine paths along which growing neurites would extend. The electrodes onto which the neurons were cultivated were used both for stimulating neurons as well as for monitoring their electrical activity.

At Caltech (California Institute of Technology), a device called a "neurochip" has been realized in which a network of live brain cells was connected through electrodes on a silicon chip to stimulation and detection circuitry [1] [2]. Neurons having a maximum diameter of about 15 μm were taken from the superior cervical ganglion (SCG) of a rat. The "neurochip" had three main features: a well formed in the silicon substrate into which a neural cell was confined, an overhanging grillwork for trapping the cell body inside the well, and an electrode in contact with the trapped neuron.

The disclosed "neurochip" was composed of sixteen trapezoidal wells, closed at the top by an overhanging grillwork of patterned heavily doped silicon, constituting a 4×4 array, realized on a silicon wafer by photolithography and "micromachining" of the silicon crystal. On the bottom face of the silicon wafer, a predefined 4×4 array of gold electrodes that closed the bottom of the wells provided a stable electrical contact with the entrapped cell bodies. The surface of the electrodes at the bottom of the wells was covered with platinum black for reducing contact impedance with the body of the neural cell.

The entrapment grillwork was designed to permit the introduction of an embryonic neural cell into each well and prevent that cell from escaping. At the same time, the grillwork allowed neurites to sprout through the apertures of the grillwork and connect to other neurons to form a live neural network.

A variety of different grillwork patterns have been tested to prevent cell escape. In a recent release of the neurochip, depicted in FIG. 1, a MEMS structure forms a sort of canopy above the well. The overhanging grillwork above the etched cavity in the silicon substrate has openings through which neurites may sprout.

FIG. 2 is a SEM (Scanning Electron Microscope) picture of the grillwork and a cross sectional schematic of the trapping well closed by the retention grillwork showing the openings through which the neuron grows and eventually develops its neurites.

The height of the openings through the grillwork (micro tunnels) depends on the thickness of the patterned nitride layer that constitutes the overhanging grillwork. An appropriate choice of the dimensions of these micro tunnels allows neurons to grow out of the well cavity, but preventing their escape. Experiments have shown that the crucial parameter in preventing neuron escape through the growth "microtunnels" is not their breadth but their extension (length), that is the thickness of the grillwork nitride layer.

However, reliable entrapment of neurons by means of an insurmountable overhanging grillwork that obstructs the well opening have the disadvantage of not allowing the replacement of dead cells without irreparably damaging the confining device.

At the "Max Planck Institute for Biochemistry" in Munich, Germany, Peter Fromherz and Gunther Zech carried out experiments on neurons of "Lymnaea Stagnalis" [3] that, being an invertebrate (a kind of slug), has neurons with a relatively large body that contact the underlying interfacing substrate very well. These neurons, even in small numbers, were capable of reproducing normal biological functions.

The neurons were cultivated onto a silicon chip, shown in FIG. 3. The letters S, G and D indicate the source, gate and drain terminals, respectively, of an integrated Filed Effect Transistor (FET). The white scale line is 20 μm long.

The chip was covered with a layer of silicon oxide for preventing electrochemical phenomena at the neuron-substrate contact surface and also for creating a homogeneous and inert rest surface for the neurons. Neurons were confined on the silicon substrate by means of a polyamide picket fence.

In order to ensure a noninvasive neuron-silicon interface, a two-way electrical coupling was established by means of the FET and a stimulator (ST). The stimulator (ST) was substantially constituted by a P doped zone onto an N doped silicon region covered by a thin layer of silicon oxide. The source and drain terminals of the transistor were realized in distinct P doped regions with a gate area covered by a thin gate oxide layer not topped by any metal gate electrode layer.

The stimulator (ST) provided a capacitive coupling between the chip and the neuron, while the transistor, integrated in the silicon under the neuron body, sensed the extracellular voltage.

FIG. 4 shows a neuron grown on the device of FIG. 3 after having been cultivated for three days. FIG. 5 is a microscope image of neural cells (dark circles) each confined by a six picket fences of polyamide. Some pickets of adjacent fences have combined, forming a single picket of elongated cross-section. The light gray lines that originate from the cells are neurites grown on the surfaces of the chip that connect the neurons among them. The radially extending straight lines are the traces of the connecting metal lines of the stimulators and sensing transistors.

By electrically exciting a neuron (via the stimulator), an electrical activity is induced in another neuron of the network that modulates the current in the transistor underneath it, thus amplifying the tenuous electrical signal. Such a detected variation of potential indicates that an electrical synapse has been established between the two neurons.

Notwithstanding the effectiveness of these devices, reliable and durable spatial confinement of the neural cells is precarious because the neurons tend to escape the picket fence.

The recurrent problem in designing these devices is to reliably prevent cell escape, but still allow cell growth, and to reliable couple the cells to electrodes (or alternate stimulation and detection means), preferably on an easily micromachinable material such as a monocrystalline silicon chip (wafer).

The fact that the confined cell may not properly adhere to the surface of the substrate and thus fail to remain in stable contact with the electrical stimulation and detection elements may impede the stimulation and the monitoring of exchanged electrical messages. The known interfacing structures discussed above represent the best compromise currently available, but better devices are still needed.

BRIEF SUMMARY OF THE INVENTION

It would be highly desirable to have a device for confining neural cells on a semiconductor chip for noninvasive microelectronic interfacing that in addition to satisfying the above discussed requisites, would also allow the substitution of any single neuron at any phase of its growth within a confinement cavity without damaging the device.

To all these important and often contrasting requisites, the present applicants have found an effective answer based on the realization of a device that includes an overhanging retention grating that, in contrast to the known "static" grillwork structures, may be elastically deformed in a reversible manner by forcing a certain electric current therethrough to uncover or widen the obstructed aperture of the well and permit introduction of a cell into the confinement cavity.

Fundamentally, the overhanging grating for retaining the growing neural cell in the confinement cavity includes at least a pair of coplanar and substantially parallel members (traverses) of conducting material, separated by a certain gap, spanning the full width of an opening of the well cavity, each terminating with at least an enlarged portion or pad, connectable to an electrical power source for forcing a current along the parallel extending members.

Depending on whether the currents in the two parallel elongated traverses flow in the same direction or in opposition directions, either a repulsive or an attractive force is induced, which flexes the portion of the portion of the two parallel conductors hanging over the opening to uncover or widen the aperture. Besides being induced by electromagnetic effect, the flexing may be also partly induced by thermal elongation of traverses spanning across the opening, as a consequence of the heating by Joule effect of the two parallel traverses having their ends suitably restrained.

The two parallel conductive elongated members of the retention grating of this invention may even deliberately have different cross sectional areas for providing different thermal elongation in the two members. Accordingly, for the same electric current circulated in series in the two parallel members, the Joule heat produced in the slender (essentially more resistive) of the two will be greater than the heat produced in the other member of much larger cross section. The augmented thermal elongation of the slender member produces axial compressive stresses that accentuate the swaying of the slender traverse in the same direction that is immediately caused by the electromagnetically induced repulsive force.

Optionally, the desired direction of swaying of the slender traverse because of the axial compressive stress due to thermal elongation may be predetermined by defining the elongated slender traverse with a slight (biasing) curvature.

According to yet another embodiment, two substantially rectilinear and parallel conductive members are defined in a way to form an elongated cantilever fork with a substantially uniform narrow separation slit between them. One of the two arms constituting the cantilever fork is made much slender than the other arm, in order to provide a different thermal elongation of the two arms upon circulating an electric current in series along the two arms of the fork. The elongated fork, including its end bridge portion, is unrestrained. The two arms extend in a cantilever manner from their respective terminal pads of relatively large areas that remain mechanically connected to the substrate through a residual electrically insulating layer, as will be better described later.

The elongated cantilever fork hangs parallel over the flat surface of the substrate, at a height of separation that may be generally comprised in the range of 0.5 to 3 µm, as appropriate for the size of the cell being studied.

Upon forcing an electric current in series along the two arms of the cantilever fork, by connecting their two end pads to a power source capable of forcing a certain current, the elongated cantilever fork grating flexes sideways uncovering the aperture or, more practically, several aligned apertures of wells, normally partly or completely occluded by the free end portion of the elongated overhanging cantilever fork grating.

The dimensions of the coplanar parallel traverses of electrically conducting material are designed to ensure that the electromechanically and/or thermal elongation induced mechanical stress does not exceed the elastic limit of the material of the traverses. The elastic memory of the material ensure the re-closing of the apertures upon ceasing to force a certain electric current along the traverses.

Electrical coupling means with the entrapped cell body for stimulating the neuron and for detecting neural activity may be embedded in the walls or at the bottom of each confinement well, according to any of the known techniques of establishing an effective electrical coupling between the trapped cell body and the stimulating and/or detecting circuitry.

For example, an appropriate stimulation/detection electrode may be arranged at the bottom of the cavity according to the arrangement illustrated in FIG. 2.

Of course, other means of establishing such a coupling, including the formation of metal-oxide-semiconductor transistor structures and integrated stimulating electrodes according to the approach disclosed in the above mentioned publication of the Max Plank Institute for Biochemistry and depicted in FIG. 3, may be implemented for electrically interfacing with the entrapped neuron.

The present device may be integrated into a semiconductor device for analyzing the functioning of live neural networks together with circuits for conveying electrical stimulating pulses to selected neurons and for detecting electrical activity of other neurons caused by the stimulation.

The above summary of the present invention is not intended to represent each embodiment or every aspect of the present invention. For example, the device can be used to study any cell type of interest. It has particular application to tissue engineering, where the arrangement of different cells types must be controlled during growth of the tissue. For example, different cell types can be directed to grow in different directions using the appropriate surface coating materials and/or the entire tissue can be appropriately seeded with neuronal pathways as needed for the tissue type. The tissue can then be released from the device using the electrical gating means described herein.

BRIEF DESCRIPTION OF THE DRAWINGS

FIG. 10 shows the two parallel traverses that compose the retention grating of FIG. 9, elastically bent sideways for widening the aperture there between.

FIG. 13 is a scheme of a system for analyzing the functioning of a live neural network cultivated on a chip of this invention.

FIGS. 14 and 15 are a cross sectional and plan view, respectively, of an alternative form of confinement cavity that may be formed in a neurochip substrate for cultivating neurons.

DETAILED DESCRIPTION OF THE INVENTION

The effectiveness of an electrically deformable retention grating has been proven using a simulation and analysis tool implementing a technique of finite element modeling and coupled multi-physics analysis. With this technique, it is possible to model a continuous body with a set of elements (finite elements). By applying appropriate boundary conditions (mechanical constraints, electrical, electromagnetic and thermo-electrical solicitations) that simulate the real environment in which the system functions, it is possible to predict the behavior of the grating to verify mechanical sturdiness, reliability and compliance to design specifications.

Figure 1:
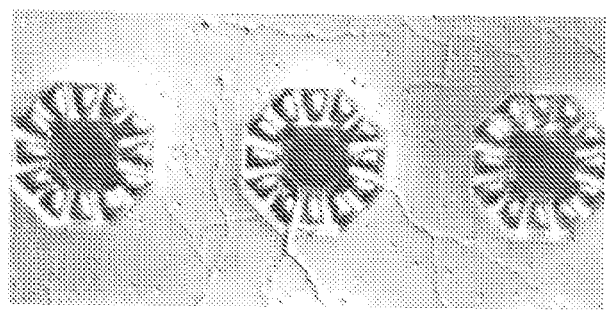
FIG. 1 is a microscope image of a "neurochip."
Figure 2:
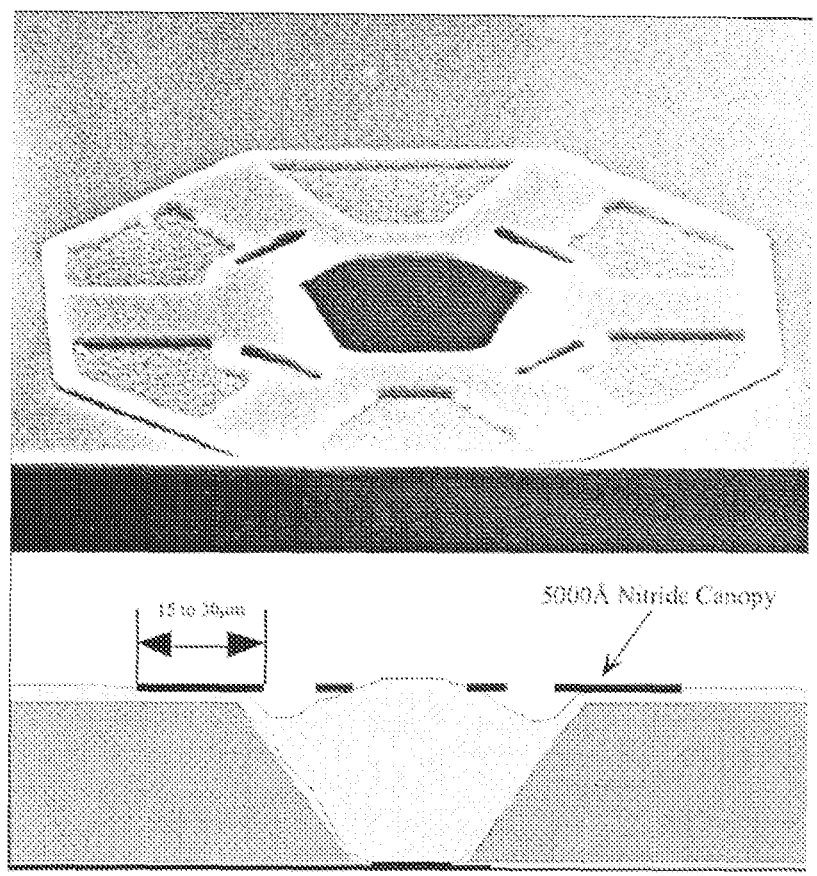
FIG. 2 shows a grillwork of a "neurochip" and a sectional view that illustrates its structure.
Figure 3:
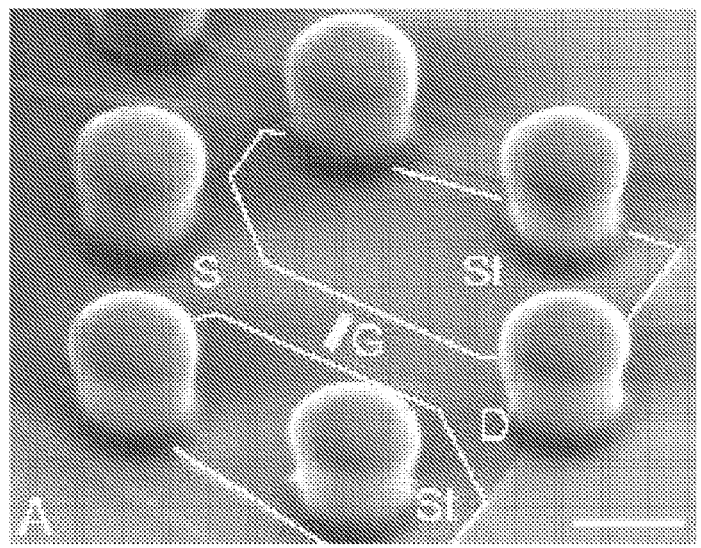
FIG. 3 is a SEM picture of a silicon substrate with picket fences of polyamide for containing a neuron.
Figure 4:
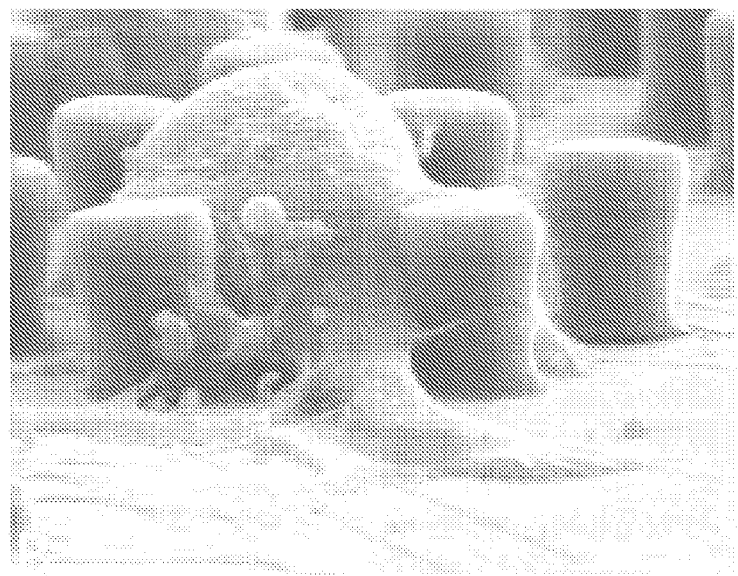
FIG. 4 is a SEM picture of a neuron entrapped by pickets of polyamide of the chip of FIG. 3.
Figure 5:
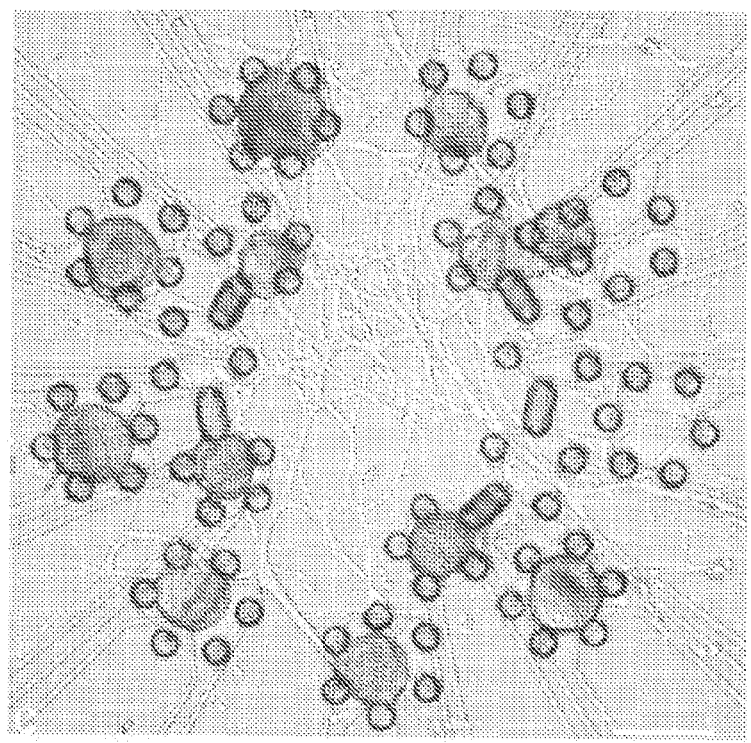
FIG. 5 illustrates the growth of neurites after two days in the culture onto a chip of FIG. 3.
Figure 6:
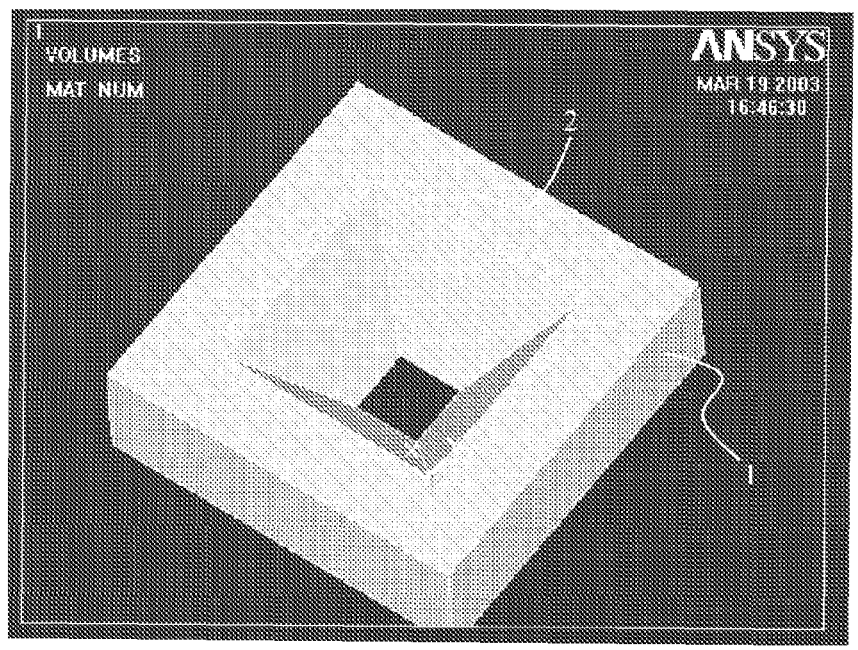
FIG. 6 shows a well cavity of a confinement device according to an embodiment of this invention.
Figure 7:
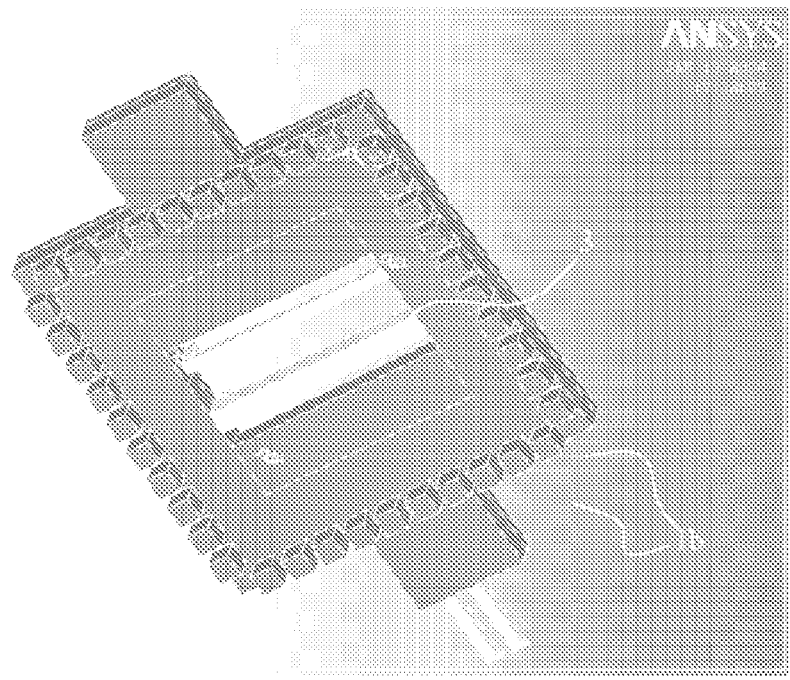
FIG. 7 is a view, from the well cavity side, of the retention grating assembly of the confinement device according to an embodiment of this invention.
Figure 8:
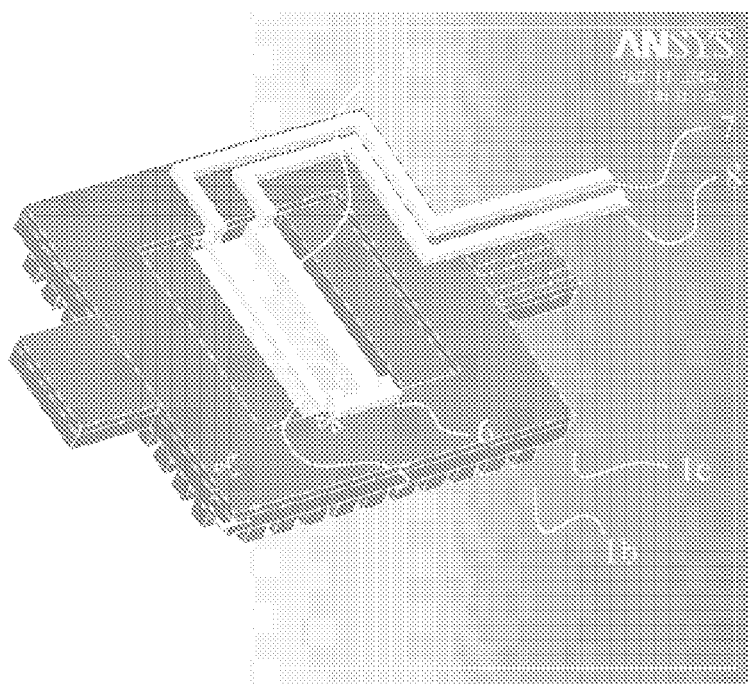
FIG. 8 shows the upper face of the retention grating assembly of FIG. 7.

Basically, the confinement device for a neural cell includes a well 2 formed in the substrate 1, a sample embodiment of which is shown in FIG. 6 and a retention grating subassembly 3, a sample embodiment of which is shown in FIGS. 7 and 8.

Both parts may be separately realized by common micromachining techniques of Bulk micromachining and of Surface micromachining and successively bonded together to form a complete spatial confinement device for cultivating neural cell.

"Bulk micromachining" techniques allow the manufacture of transducers, interfacing microdevices and special components by electrochemically excavating a monocrystalline silicon substrate.

With these sophisticated fabrication technologies it is possible to control accurately the dimensions and the form of cavities produced even at buried locations in a silicon substrate by controlling the progression of selective channel and/or electrochemical etching.

In the sample embodiment of FIG. 6, the well 2 produced in or through a silicon substrate chip 1, has a truncated-pyramidal shape, but it may be realized even in other shapes by using anisotropic etching techniques.

The well cavity 2 may be anywhere between 10 µm to 40 µm deep, the area at the truncated bottom may range from 30 µm$^2$ to 400 µm$^2$, and the area of the well opening may range from 400 µm$^2$ to 3000 µm$^2$. These dimensions are generally suitable for the confinement of neural cells that are normally used in neural network studies and for promoting a stable contact of the trapped neuron body with the bottom of the well that, in the embodiment shown, has an electrode 4 for stimulating the neuron and sensing electrical activities of the trapped cell.

In contrast to "Bulk micromachining" techniques, the so-called "Surface micromachining" techniques, such as the technique used for realizing the overhanging retention grating 3 of FIGS. 7 and 8, are additive processes by which functional features of the structure are realized over the surface of the silicon substrate.

An electrically deformable retention grating of this invention may be separately fabricated on a thin silicon slice 1 c in the form of the subassembly depicted in FIGS. 7 and 8, that may then be bonded over the thicker silicon substrate of the neurochip, in juxtaposition with a well already formed therein. The fabrication sequence avails itself of common fabrication steps such as: depositing a layer of insulating silicon nitride over the silicon surface; depositing a thin sacrificial oxide layer over the deposited nitride layer; defining by photolithography the desired grating elements; depositing a layer of conductive polycrystalline silicon ("polysilicon" or briefly "poly"); and selectively etching the oxide.

FIG. 8 shows the patterned metal lines 7 and 8 for electrically connecting the two traverses of conductive polysilicon 5 and 6, constituting the retention grating 3, to an electrical power supply capable of forcing through the traverses a certain electric current that will flow in opposite directions along the two arms of the fork structure of the grating.

Figure 9:
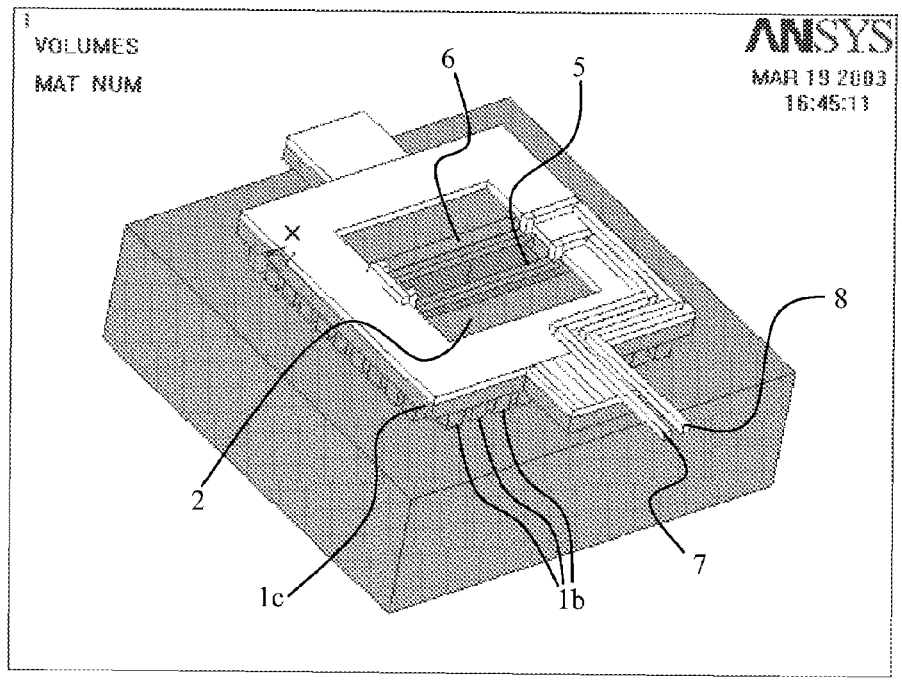
FIG. 9 is a view of a complete confinement device composed of a well covered with an electrically deformable overhanging retention grating assembly.

A view of a single confinement device realized on a neurochip made according to a first embodiment of this invention is shown in FIG. 9. As depicted, the electrically deformable retention grating subassembly rests on a plurality of perimetral legs 1b, in the form of cubes of about 1 µm side defined by masked etching of the rear surface of the thin silicon slice 1c, on which the retention grating structure is separately fabricated. The bases of the cubes are eventually bonded to the surface of the substrate 1 of the neurochip to fix the overhanging electrically deformable retention grating over a respective confinement well 2. The spaces of about 1 µm between adjacent legs 1b, aligned along the whole perimeter of the overhanging structure, provide innumerable radially extending channels of about 1×1 µm cross section, through which the confined neuron may extend processes and neurites over the surface of the neurochip to eventually establish synapses.

Figure 11:
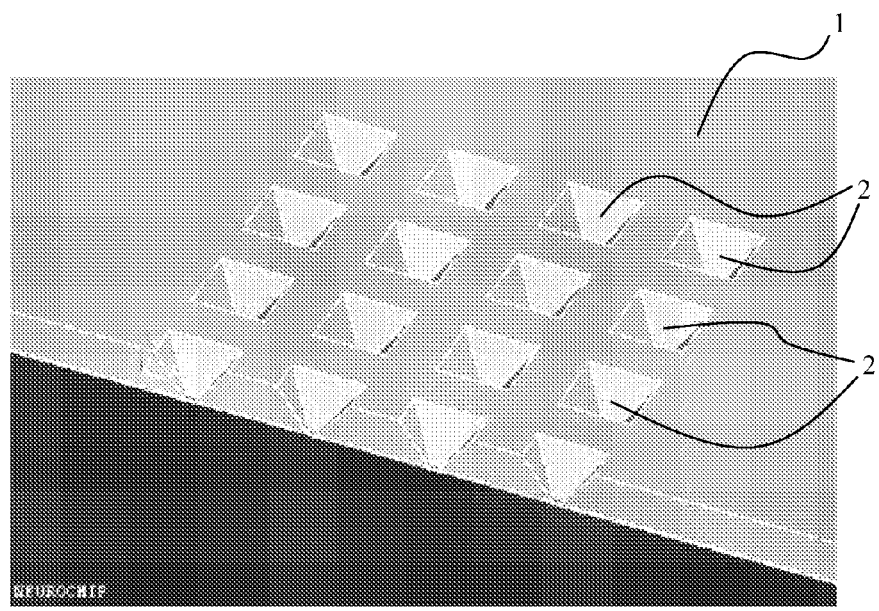
FIG. 11 shows an array of wells formed in the substrate of the neurochip.

The neurochip will include an array of confinement devices of FIG. 9 formed on the monocrystalline silicon substrate 1, for example according to a spatial arrangement of the relative wells 2 shown in FIG. 11.

According to the embodiment illustrated in FIGS. 6-12, the two extremities of the parallel traverses 5 and 6 of conductive polysilicon, forming the electrically deformable retention grating, are restrained at both their ends and are electrically connected at one extremity by a conductive bridge portion of polysilicon. Such a preferred arrangement forces an electric current serially along one traverse and back along the other traverse through metal lines 7 and 8, connected to an electric power supply.

Figure 10:
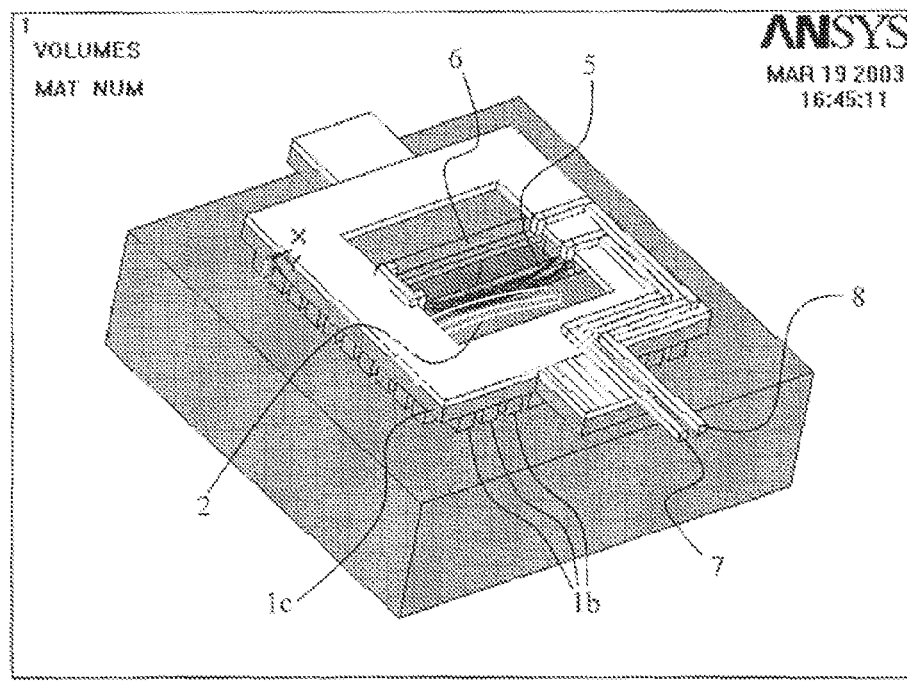

Referring to the illustrations of FIGS. 9 and 10, the different conducting cross sectional areas of the two parallel traverses 5 and 6, in which the same electric current flows in series, determines a stronger heat generation by Joule's effect along the slender (essentially more resistive) traverse 5 and the compressive stress eventually causes an accentuated swaying (sideway bending) of the slender traverse 5 away from the other traverse 6 because of the induced repulsive force between the two conductors (traverses) crossed by electric current in opposite directions.

It is also possible to predetermine the direction in which the slender traverse 5 will sway by defining it with a slight curvature that will be accentuated by the thermal elongation compressive stress.

In any case, the aperture defined by the grating is widened by forcing a current through the structure, the widening being sufficient to permit introduction of an embryonal neuron cell into the well cavity 2, under the deformable retention grating 3.

Naturally, the footprint of the retention grating 3 on the opening area of the confinement well 2 will be designed such to leave relatively narrow apertures for permitting the neuron to sprout processes and neurites out of the confinement trap eventually connecting with other neurons to form a live neuronal network over the neurochip substrate.

Alternatively, the electrically deformable retention grating 3 may be directly fabricated over the well aperture by a fabrication process similar to the one described in [1] or in [4].

Thermal elongation coefficient in polysilicon is about 2.5 PPM/° C. and the thickness of the polysilicon layer from which the two traverses are patterned, may range from 1 µm to 10 µm and have a width ranging from about 0.2 µm to 5.0 µm.

By proper design, the mechanical stresses that are induced in the traverses that form the retention grating of this invention, will be limited within a maximum value such to remain safely below the elastic limit of the constituent conductive material (e.g. doped polysilicon) in order to ensure the return of the elastically deformed traverses to their original form and dimensions upon interrupting the flow of the electric current. This is accomplished by properly designing the cross sections and form of the overhanging traverses in function of a certain design current to be forced therethrough to cause their swaying.

Figure 12:
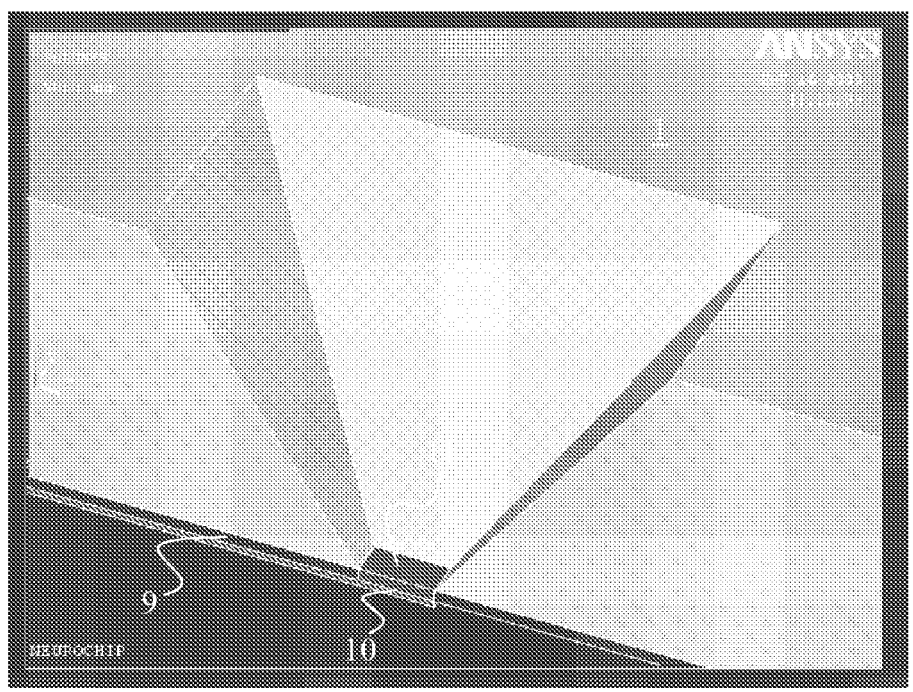
FIG. 12 is a detail sectional view of a well of the array of FIG. 12, showing the stimulation/detection electrode at the bottom of the well cavity.

FIG. 12 shows how a stimulating/detecting electrode 4 may be embedded in the cavity or well 2 of the confinement device according to the embodiment illustrated in the preceding figures. Bulk micromachining of the monocrystalline silicon substrate is continued until etching through the whole thickness of the substrate and an electrically insulating silicon nitride layer 9, deposited over the back surface of the silicon wafer, and over which is deposited a layer of gold 10, practically stopping the etching on the deposited and already patterned gold layer 10. The contact surface is preferably coated with a platinum layer 11 and the so realized electrode at the bottom of each well cavity is connected through the patterned gold lines 10 to the stimulating circuitry and to the detection circuitry.

For further reducing the electrical contact impedance with the neuron body entrapped in the well, the contact surface may also be provided with a top coating of platinum black.

A neurochip analyzer with a functioning of a neural network is schematically shown in FIG. 13. Each stimulation/detection electrode formed at the bottom of truncated pyramid confinement wells according to the embodiment described above is connected to an interface circuitry with a neuronal stimulating unit and to the interfacing circuitry with a monitoring unit of electrical activities of the neurons.

The electrically induced swaying of elongated traverses may be practiced according to alternative embodiments. For instance, instead of relying on a sideways bending of elongated traverses spanning across the aperture of the confinement cavity and mechanically restrained at both ends onto the surface of the substrate, under the action of electromagnetic attraction or repulsion force and/or of axial stresses caused by thermal elongation of the parallel conducting members mechanically restrained at both ends, the same result may be achieved by relying on the swaying on the plane of a cantilever elongated fork grating.

The cantilever fork grating may be composed of a slender am and a much wider aim connected at their free end by a bridge portion, the arms of the fork grating being restrained only at their feedthrough electrical connection pad extremities, which are the only parts solidly fastened onto the surface of the substrate.

Upon forcing a current along the two parallel arms of the cantilever fork grating, the different thermal elongation of the two arms of different conducting cross section causes the elongated cantilever fork to sway sideways on the plane of overhang over the surface of the neurochip substrate bending toward the quadrant contiguous to the arm of larger cross section.

According to this alternative embodiment, the cantilever grating is made relatively long, the portion farther away from the retraining pads (that is the free end portion) overhanging over a plurality of aligned openings of as many confinement cavities produced in the substrate. Thus, at rest, the cantilever fork grating occludes substantially all of the openings, although remaining spaced from the surface of the substrate by a distance of about 1 μm to permit neurites to grow out of the occluded opening, passing underneath the overhanging cantilever grating, and spread out over the surface of the substrate to connect with other spatially confined neurons.

According to this alternative embodiment of the invention, the confinement well is preferably in the form of a "buried" cavity that is produced with a generally ellipsoid shape at a depth of about 10 μm from the surface of the substrate. An access hole of generally square cross section with side of about 8 μm is formed by dry etching the silicon at the center of the buried cavity to be formed. The access hole is used for electrolitically etching selectively the p+ domains of a p+ doped buried epitaxial layer grown on the n-type substrate, and successively, to remove the previously oxidized porous silicon residue left by the selective electrolytic etch, by wet chemical leaching of the oxidized porous silicon mass, thus realizing an open buried confinement cavity suitable for hosting an embryonal neuronal cell.

A certain number of aligned openings of as many confinement cavities formed in the substrate are eventually occluded by an elongated cantilever fork grating overhanging above the openings, which may be caused to bend sideway sufficiently to shift its free end portion off the openings, which are then accessible by a suitable neuronal cell introduction tool.

Figure 14:
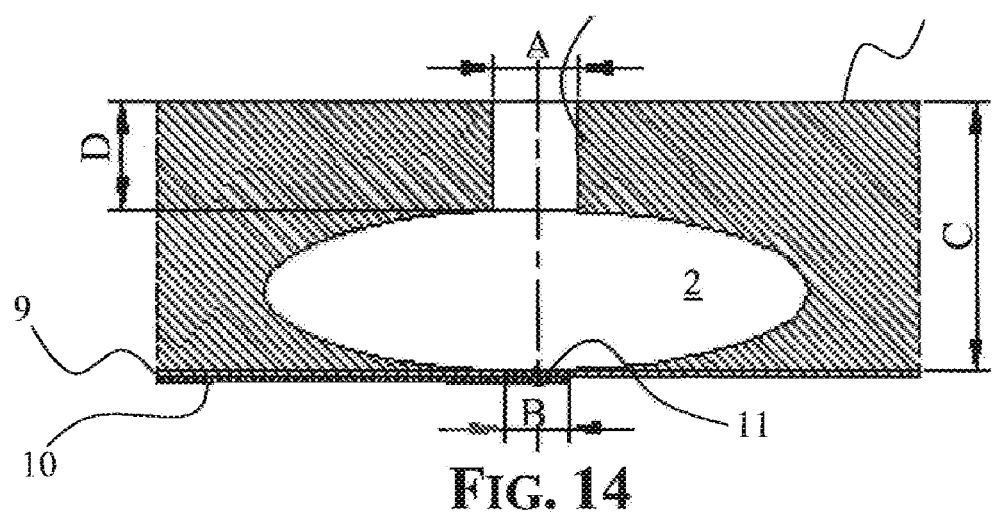

FIGS. 14 and 15 shows a sample design of a single confinement cavity 2 formed in a substrate 1 and having a central opening 2'. The indicated dimensions may be for example: A=8 μm; B=6 μm; C=25 μm; D=10 μm; E=F=70 μm. Optionally, numerous holes 11 of relatively small diameter may be etched from the surface of the substrate down to the confinement cavity uniformly distributed around the central access opening 2' to offer possible routes through which the neuron may sprout.

Electrical coupling of the confined neuron body with the stimulation/detection may be established, as shown in FIGS. 14 and 15, in the same manner as in the prior embodiment, by embedding a platinum electrode 11, preferably coated with platinum black, in the substrate 1 at the bottom of the buried confinement cavity 2, connected by patterned gold lines 10, defined on the bottom surface of the substrate over an insulating layer of silicon nitride 9.

The buried microcavities into which a neurocell is cultivated may be realized by bulk micromachining a silicon substrate that includes epitaxially grown layers purposely doped with different types of dopants and/or with different concentration of dopant.

Figure 16:
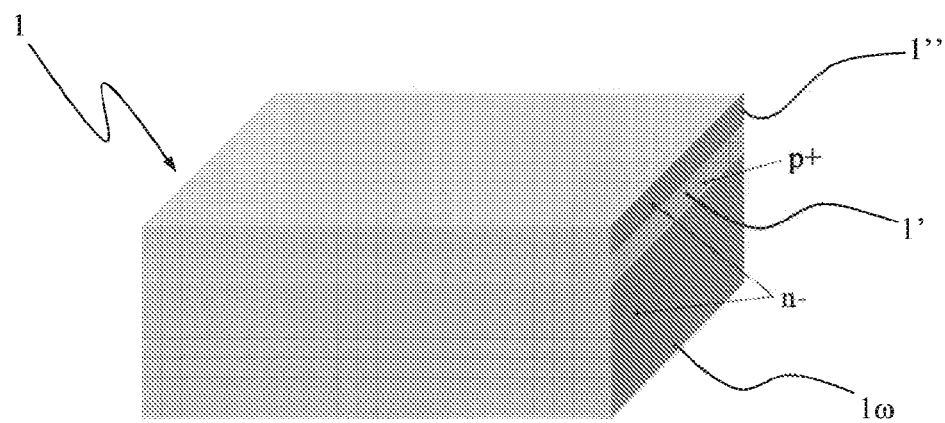
FIG. 16 shows the constitution of a silicon substrate in which buried cavities as the one depicted in FIGS. 15 and 16 may be formed by special bulk micromachining techniques.

Preferably, as shown in FIG. 16, a suitable monocrystalline silicon substrate includes a starting wafer 1w of $n^-$ doped silicon, onto which is firstly grown an epitaxial layer 1' of $p^+$ doped silicon of thickness coinciding with the height of the buried cavity to be created, for example of about 15 μm, onto which a second epitaxially grown layer 1" of $n^-$ silicon is successively grown.

The buried $p^+$ silicon layer between $n^-$ silicon is anodically etched using an electrolytic solution of hydrofluoric acid. The selectivity of anodic dissolution of silicon rests on the different contact potential (half cell potential) that is strongly dependent on the type and concentration of the dopant.

Figure 17:
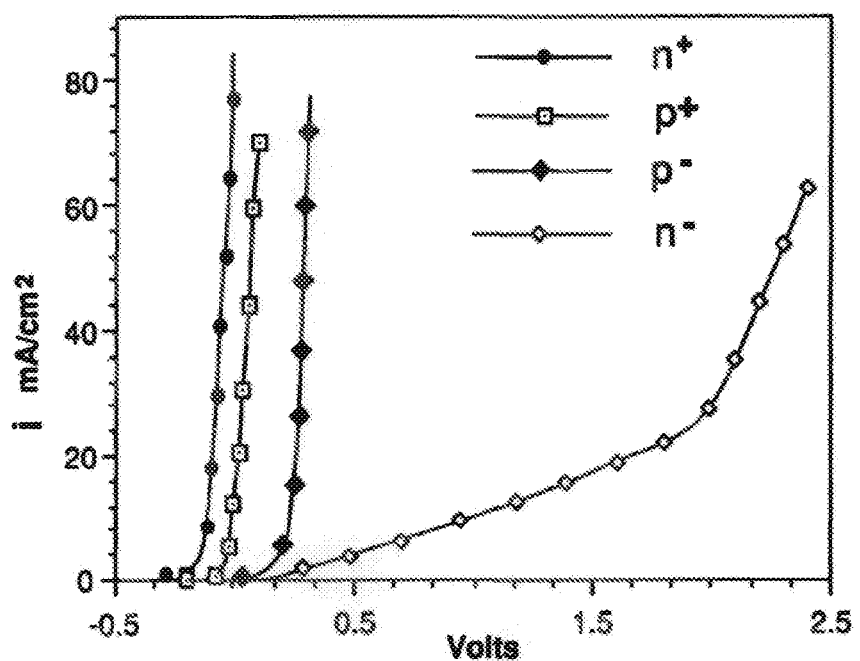
FIG. 17 shows the differences of electrochemical half-cell voltage depending on the conductivity type and concentration of the dopant, in an acid electrolyte solution used for selectively etching silicon domains having a certain dopant concentration.

FIG. 17 shows the differences of half-cell potential between a hydrofluoric acid electrolyte and silicon upon varying the type of dopant (p or n) and its concentration. The selective electrolytic etching process produces porosities in the silicon practically leaving a highly porous residual oxidized silicon structure in the region progressively reached by the electrolytic solution.

Figure 18:
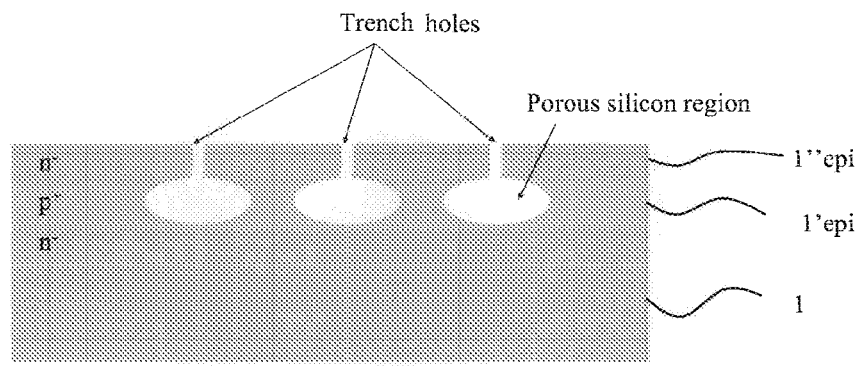
FIG. 18 shows the formation of trench holes reaching down to the p+ buried epitaxial layer for electrolitically etching the p+ silicon.

The electrolytic etching of selected buried regions of the silicon substrate may be made possible for example by forming holes (trench holes) sufficiently deep to reach down to the middle of the buried $p^+$layer at the desired locations, so that the electrolytic etching solution may reach it, as depicted in FIG. 18.

Figure 19:
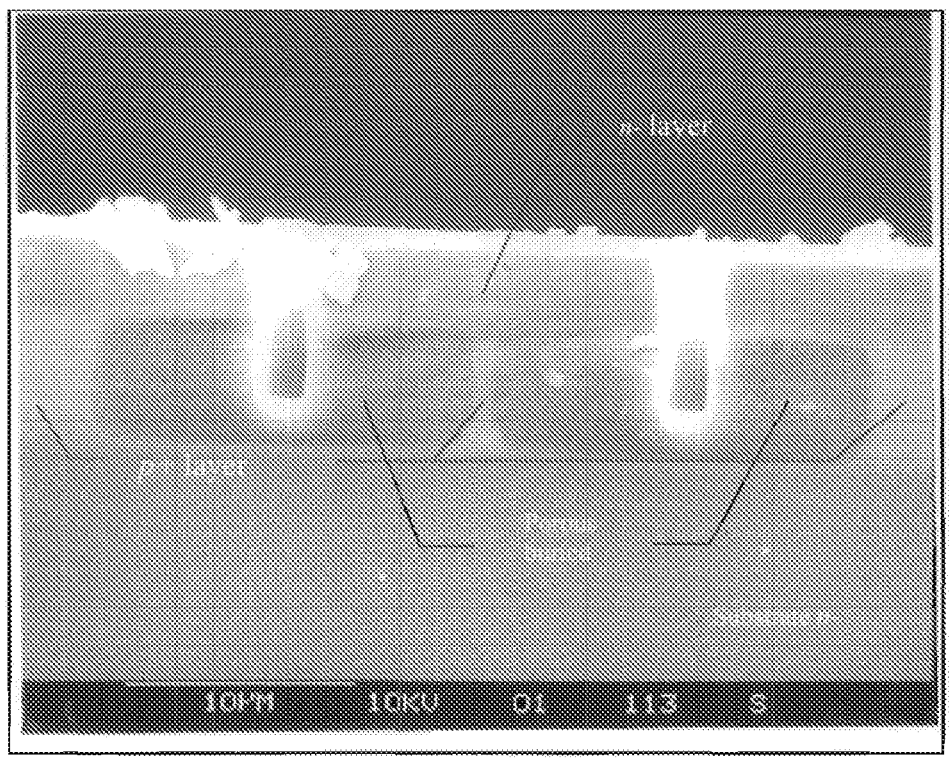
FIG. 19 is a SEM picture of the ongoing selective etching of the p+ silicon.

FIG. 19 is a SEM picture of the ongoing electrolytic erosion of the buried layer of p+ silicon, through access holes. A subsequent thermal treatment in an oxidizing atmosphere will promote a substantially complete oxidation of the highly porous residual mass of silicon in the cavity ready to be finally leached away in a KOH solution for emptying the cavity, producing a structure such as the one schematically depicted in FIG. 20. The single cantilever retention grating, according to this alternative embodiment of the invention, acts primarily by thermal elongation in function of the Joule's heat produced by forcing a current along a cantilever fork structure composed of two arms of conductive polycrystalline silicon.

Figure 21:
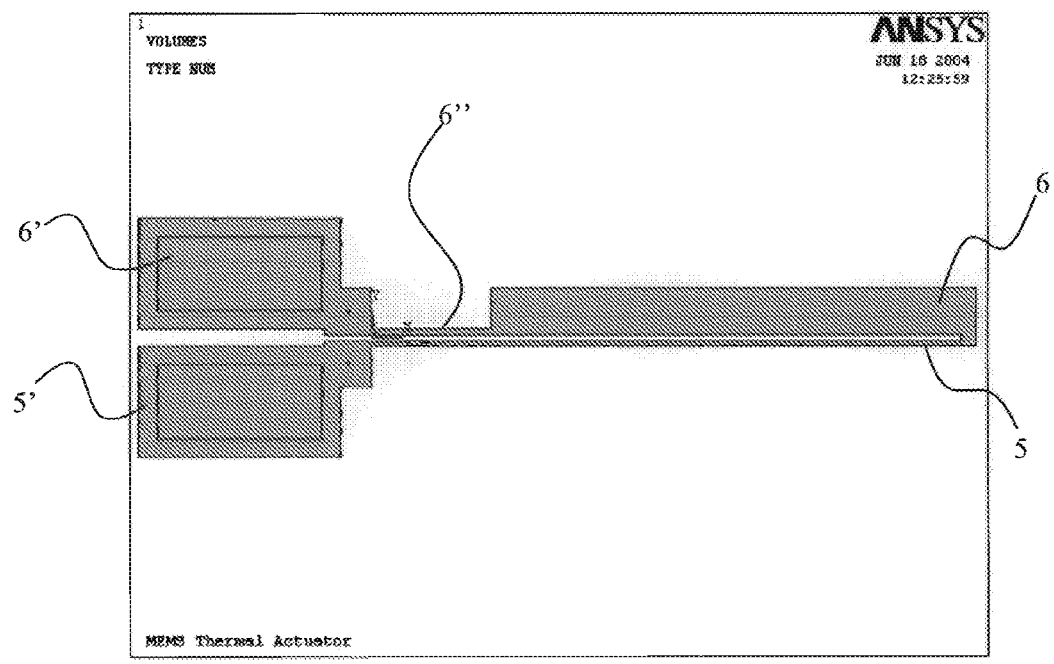
FIGS. 21 and 22 are respectively a layout view and an isometric view of a retention grating of a confinement device, according to an embodiment of this invention.
Figure 22:
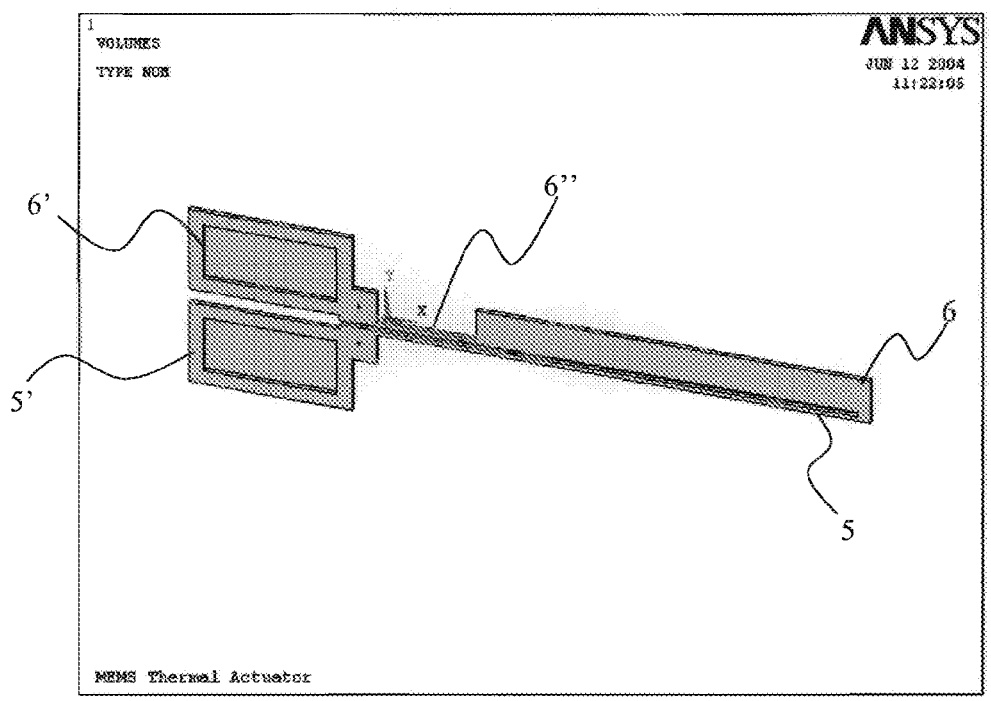

FIGS. 21 and 22 are a layout and a perspective view of a single electrically deformable retention grating (microactuator), according to this alternative embodiment. The structure is restrained only in correspondence of the two enlarged pad portions 5' and 6'. The cantilever fork portion is constituted by a pair of elongated arms 5 and 6 of conductive polysilicon joined together at their free end. The arm 6 has a larger width than the slender arm 5 for a substantial portion of its length, only a neck portion near the respective pad 6' being made as slender as the parallel arm 5, in order to provide for a neck zone of reduced mechanical resistance to bending stresses 6".

Figure 23:
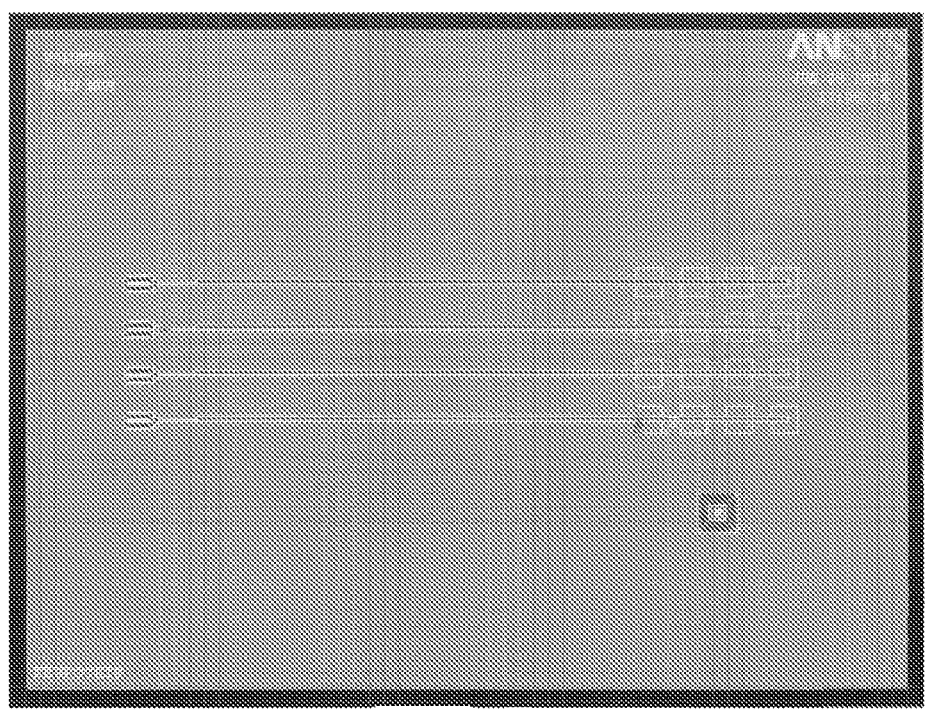
FIGS. 23 and 24 are respectively a layout and an isometric view showing the elongated retention gratings (microactuators), each extending over a plurality of aligned openings of buried confinement cavities formed in the neurochip substrate.
Figure 24:
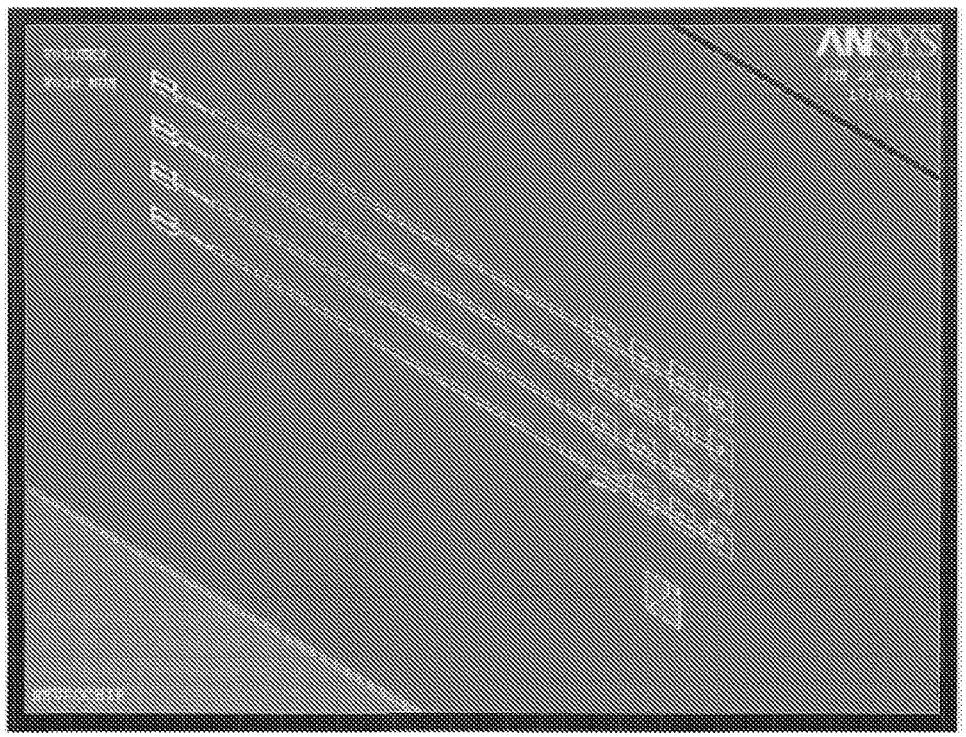
Figure 25:
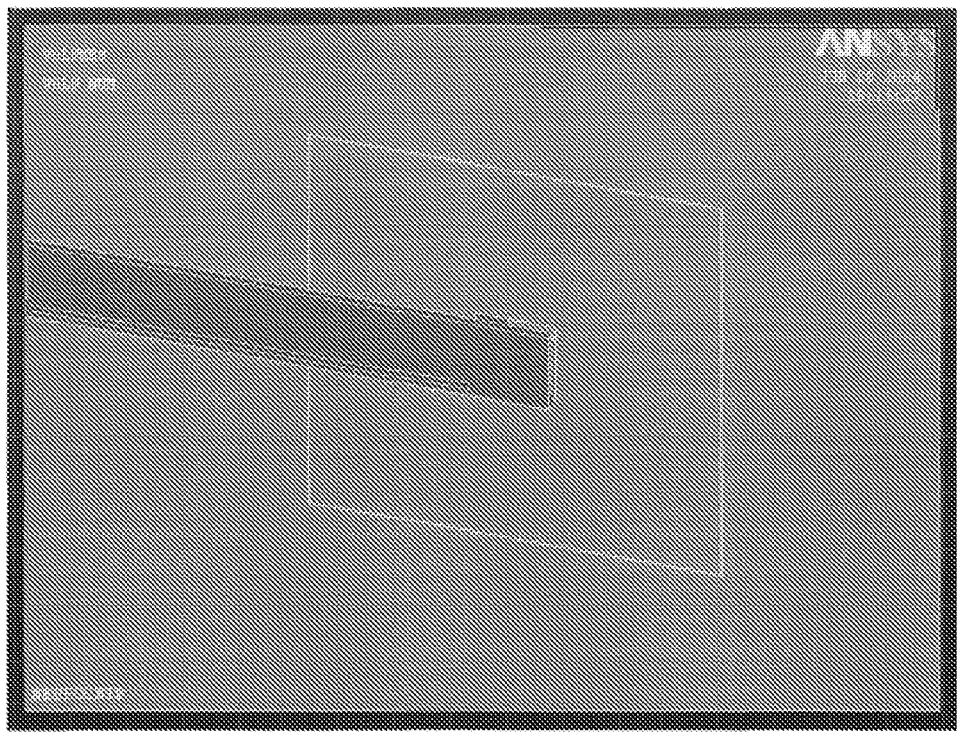
FIG. 25 is a partial enlarged isometric view of the free end of a microactuator grating occluding the opening of a confinement cavity formed in the neurochip substrate.

As schematically shown in FIGS. 23, 24 and 25, a neurochip will normally have an array of buried cavities 2, each having an opening. Each elongated cantilever grating (microactuator) 3 of conductive polysilicon is defined such that its free end portion occludes the central openings 2' of a number of aligned buried cavities 2 formed in the neurochip substrate 1.

FIG. 25 is an enlarged detail view of a farthest opening 2' that is occluded by the free end tip of the microactuator 3. According to this embodiment, the length of the cantilever arms 5 and 6 of each microactuator is 912 μm, the width of the slender arm 5 and of the neck portion 6" of the wider arm 6 is 1 μm and the thickness of the patterned polysilicon layer constituting the microactuator grating 3 is 1 μm. The neck region 6" has a length of about 60 μm. The width of the wider arm 6 is 6 μm. The size of the pads 5' and 6' is 43.5×12×1 μm. Under each of the two pads 5' and 6' there is an electrically isolating layer of silicon nitride, the dimension of which are of about 40×8×1 μm, that mechanically connect the polysilicon to the surface of the silicon substrate 1. In practice, the elongated cantilever fork microactuator composed of the two arms 5 and 6 is spaced from the surface of the substrate by about 1 μm.

Figure 26:
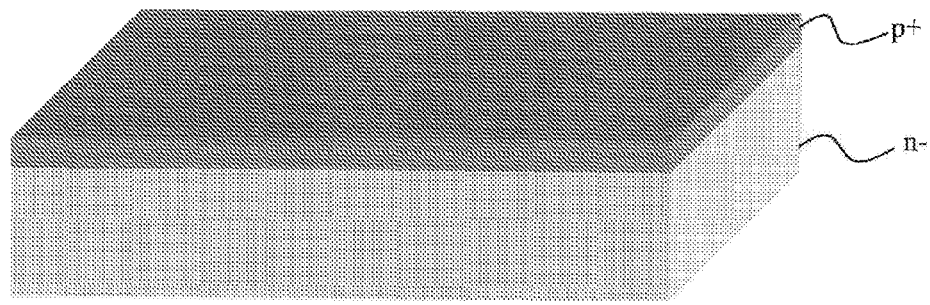
FIGS. 26-42 illustrate the process of fabrication of a neural cell confinement device according to an embodiment of this invention.
Figure 27:
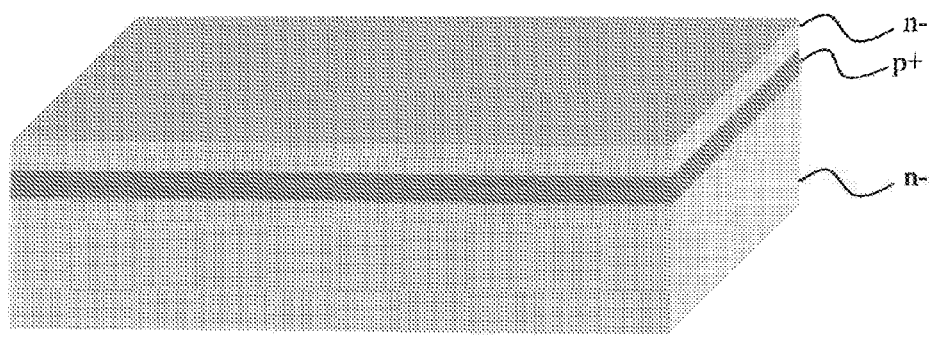
Figure 28:
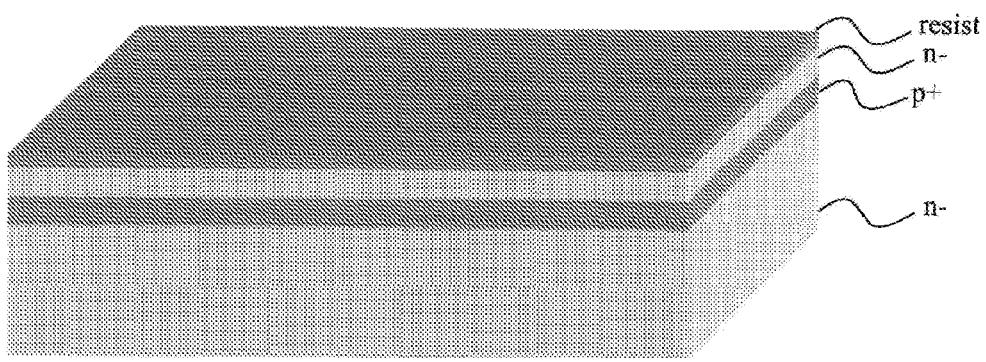
Figure 29:
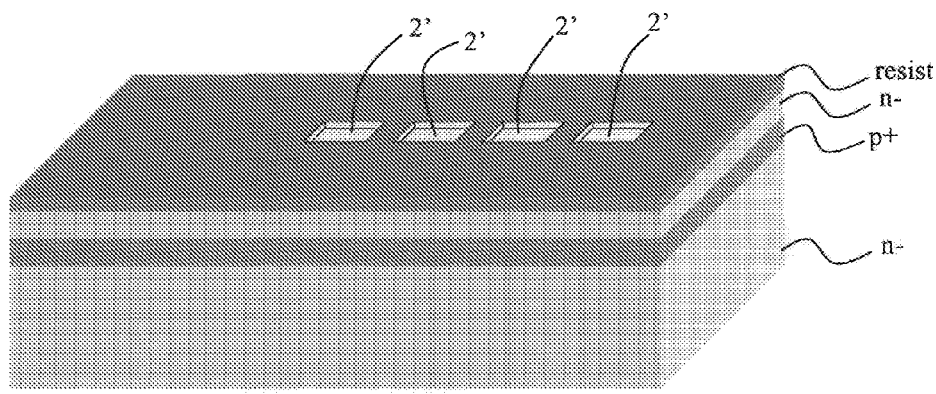

The process flow for fabricating a neurochip according to this embodiment starting from a monocrystalline silicon wafer is illustrated in the series of FIGS. from 26 to 42. FIGS. 26 and 27 show the successive epitaxial growth of a p+, layer and successively of an n− layer for constituting the silicon substrate 1 of the neurochip. FIGS. 28 and 29 show the deposition of a layer of photoresist (resist) and the photolithographic definition of apertures 2' of a generally square form through the resist mask.

Figure 20:
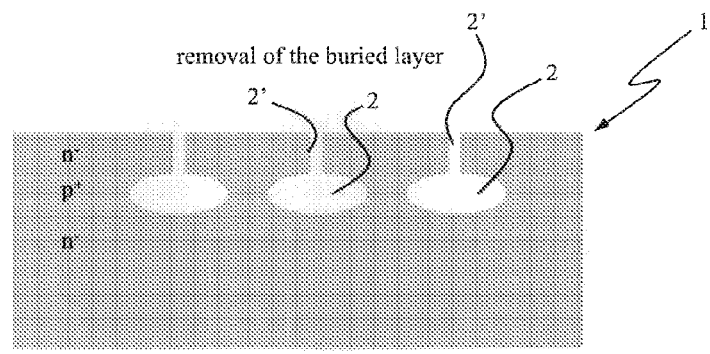
FIG. 20 shows the structure after leaching with KOH solution the porous oxidized silicon residue of the electrolytic etching.
Figure 30:
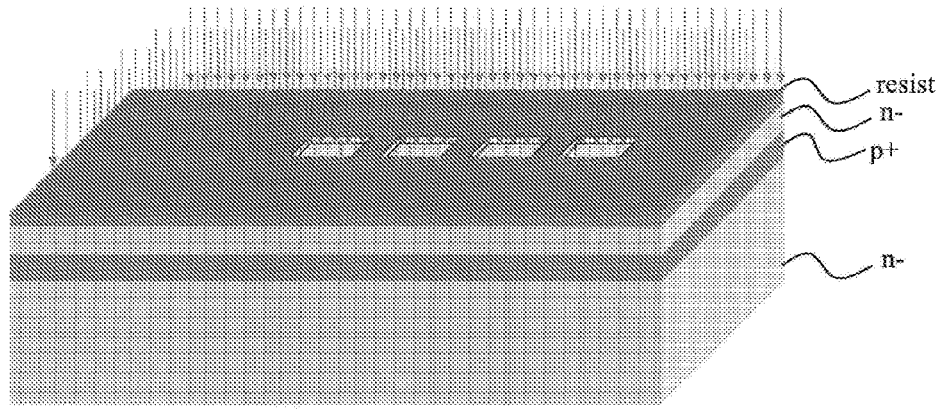
Figure 31:
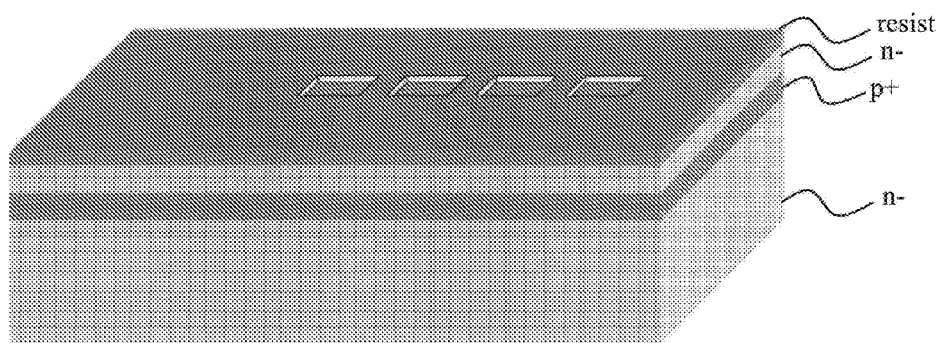
Figure 32:
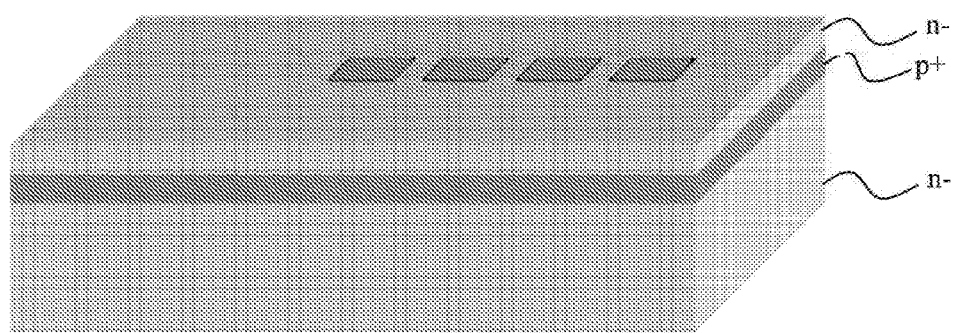
Figure 33:
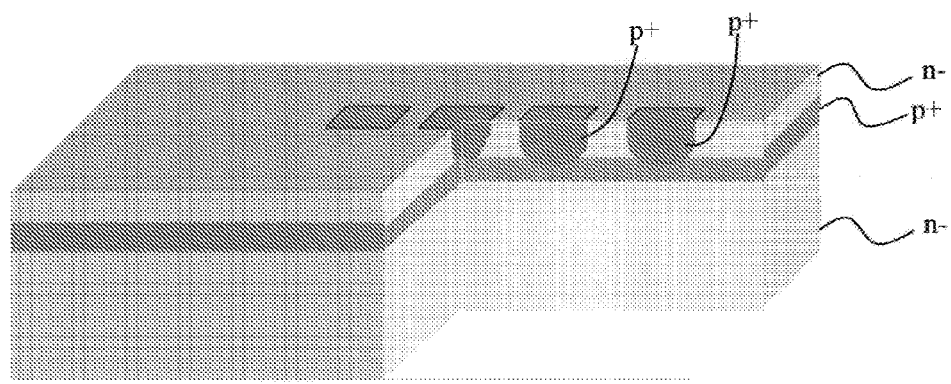

In a preferred alternative to forming access holes as previously described in relation to FIGS. 18, 19 and 20, a p+ dopant implantation is performed in the n− silicon under the square apertures of the resist mask, as depicted in FIGS. 30 and 31. FIGS. 32 and 33 show the resulting structure after having removed the resist mask. As visible in the partly cut away view of FIG. 33, the heavy p+ dopant implanted regions extend down to merge with the buried epitaxial p+ silicon layer.

Figure 34:
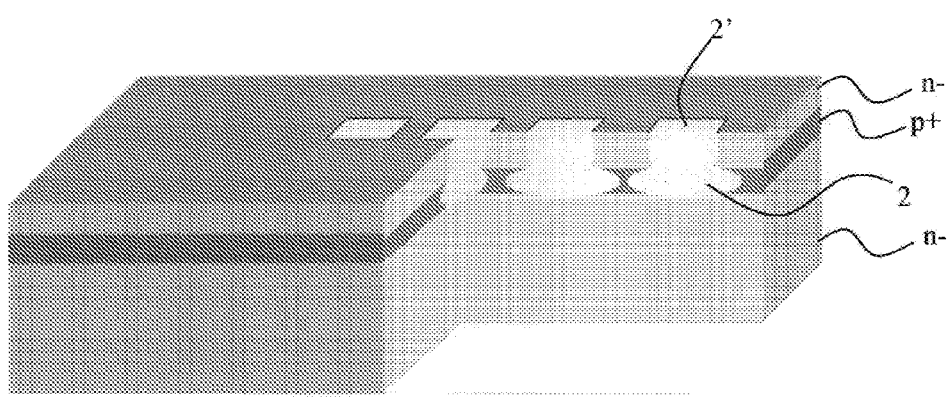

FIG. 34 is a partial cut away view showing the resulting structure after having completed the electrolytic selective etching of the p+ domains of the crystalline silicon, leaving the electrolytically etched regions of the would be buried ellipsoid cavity 2 and of the communicating channel of generally square cross section 2' in the form of a highly porous and partly oxidized residual silicon structure.

Figure 35:
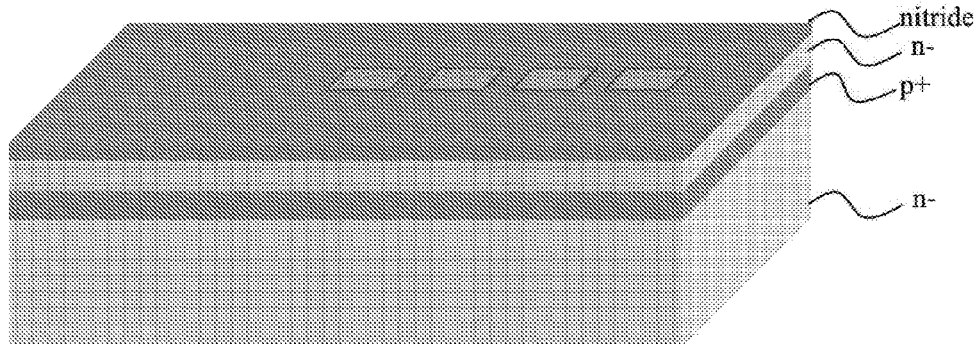
Figure 36:
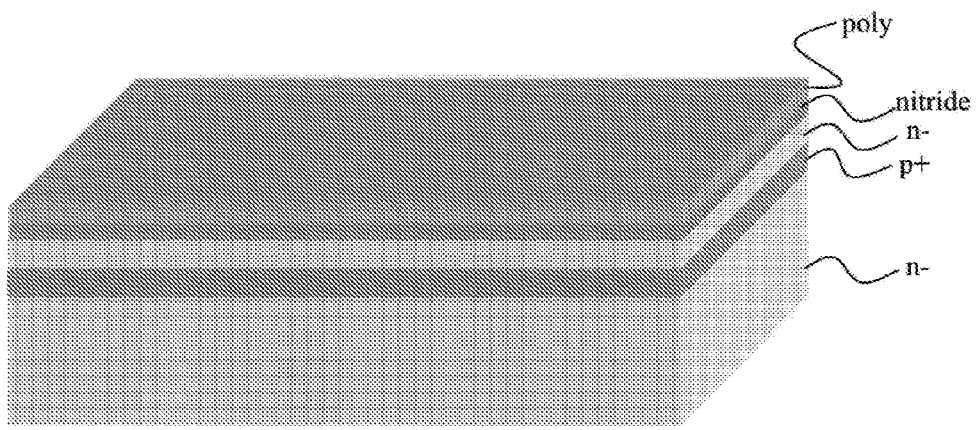
Figure 37:
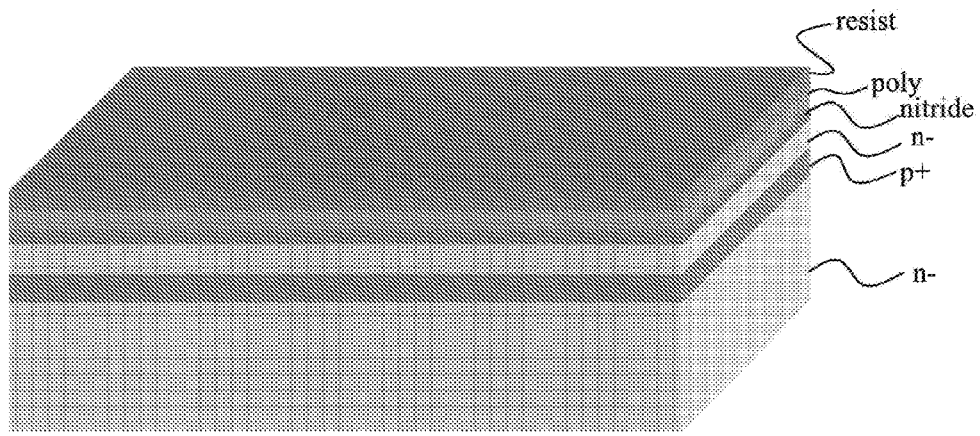
Figure 38:
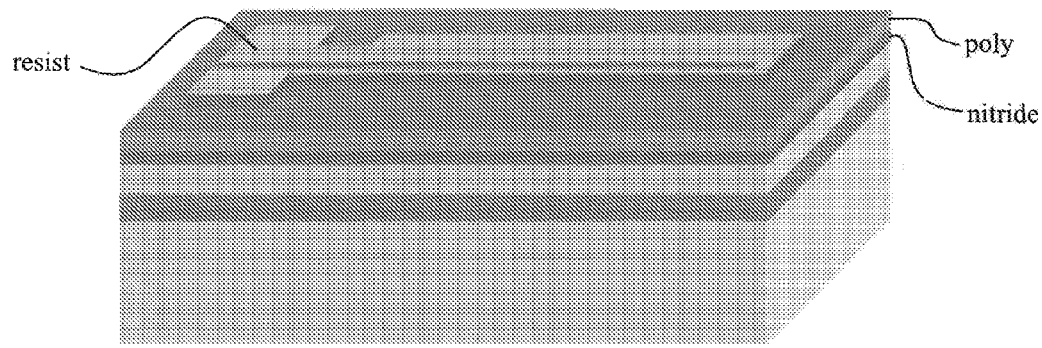

Thereafter, as depicted in FIGS. 35 and 36, a layer of silicon nitride (nitride) is deposited over the whole surface and on the nitride layer a conductive polycrystalline silicon layer (poly) is deposited. Then on the surface of the wafer a new layer of photoresist is deposited and photolithographically defined to leave the resist mask of the grating as shown in FIGS. 37 and 38 over the polysilicon layer.

Figure 39:
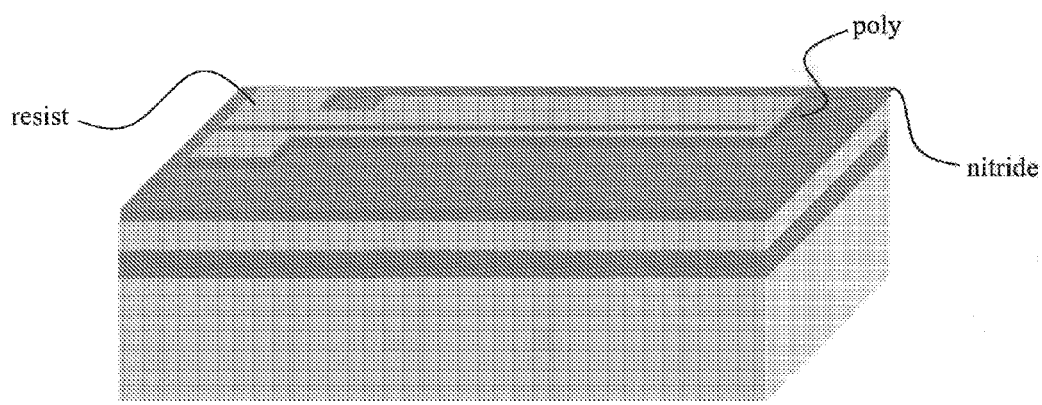
Figure 40:
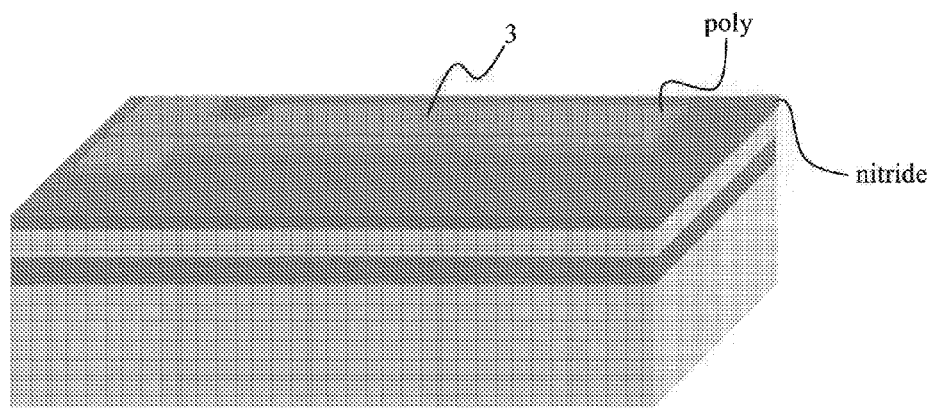

The polysilicon is chemically etched to geometrically define the electrically conductive microactuator structure 3, as depicted in FIG. 39. Thereafter, the resist mask is removed leaving the patterned microactuator structure 3 completely defined as shown in FIG. 40.

Figure 41:
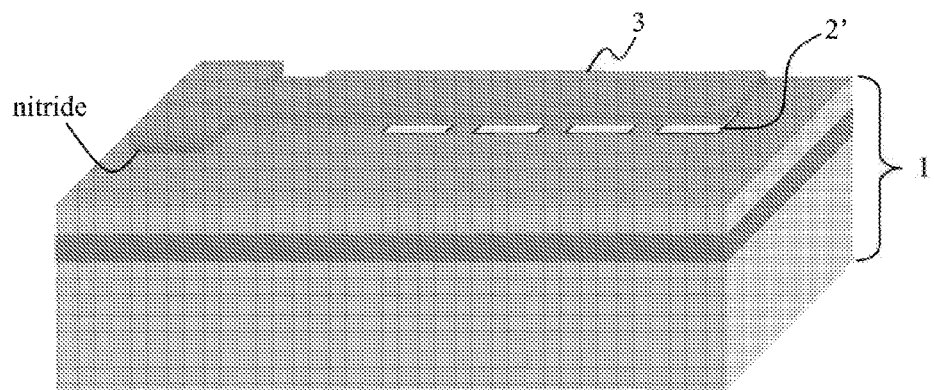

Thereafter, a controlled chemical etching with a hydrofluoric acid solution of the nitride is conducted, as illustrated in FIG. 41, so that the exposed nitride and the nitride present under the extended fork portion of the microactuator is completely removed leaving the fork portion cantilevering above the underlying substrate while, by virtue of the relatively large areas of the two pad portions 5' and 6' of the two arms of the fork structure 3, the etching of the nitride encroaches only for a short distance under the polysilicon of the two pads 5' and 6'. Indeed, by the time the nitride under the elongated relatively slender fork portion is completely removed, the etching has only marginally encroached under the definition edges of the relatively large area pad portions. By timely interrupting the chemical etch of the nitride, a consistent portion of mechanically restraining nitride layer will remain under the pad portions of the cantilever polysilicon microactuator.

Figure 42:
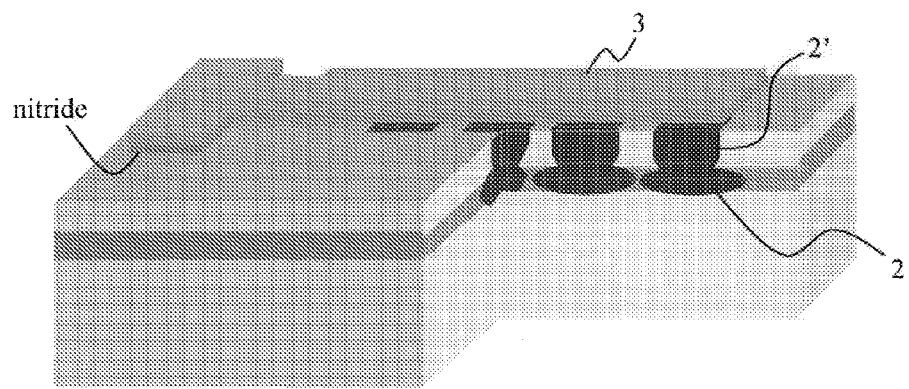

After this step of wet chemical etching of the nitride, the openings 2' of the buried cavities under the overhanging cantilever fork of the microactuator are uncovered and a final wet leaching in a KOH solution removes the mass of oxidized porous silicon residues in the whole cavities and the final structure of the entrapment device is as depicted in the partly cut away view of FIG. 42.

Figure 43:
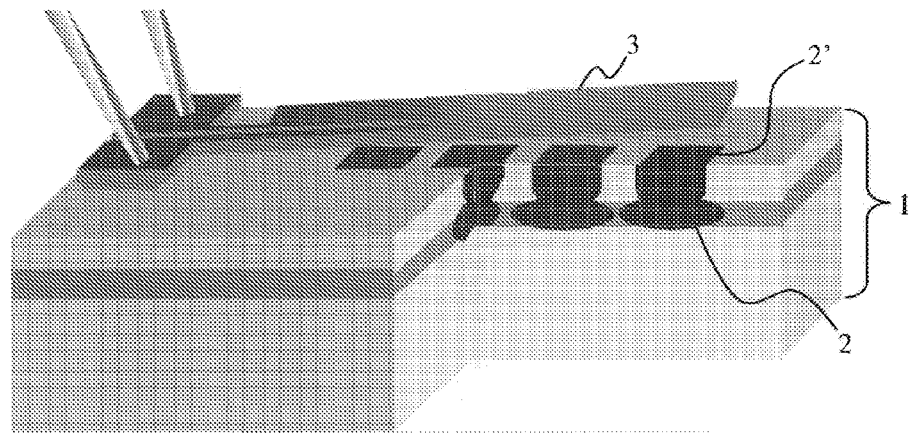
FIGS. 43-45 illustrate how several aligned apertures, completely or partly occluded by the overhanging cantilever grating (microactuator) may be completely opened by electrically forcing a sideway sway of the elongated cantilever grating for introducing neural cells in respective wells of the neurochip. The cells remain confined therein by returning the overhanging cantilever grating to its rest position.
Figure 44:
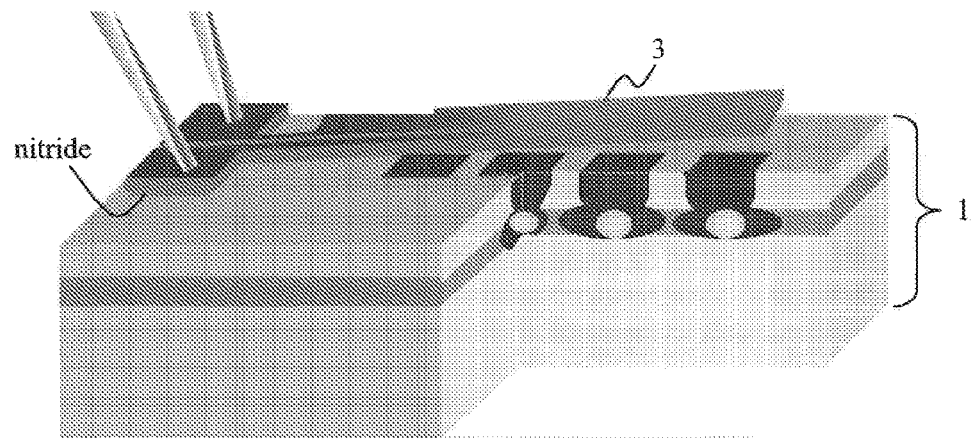
Figure 45:
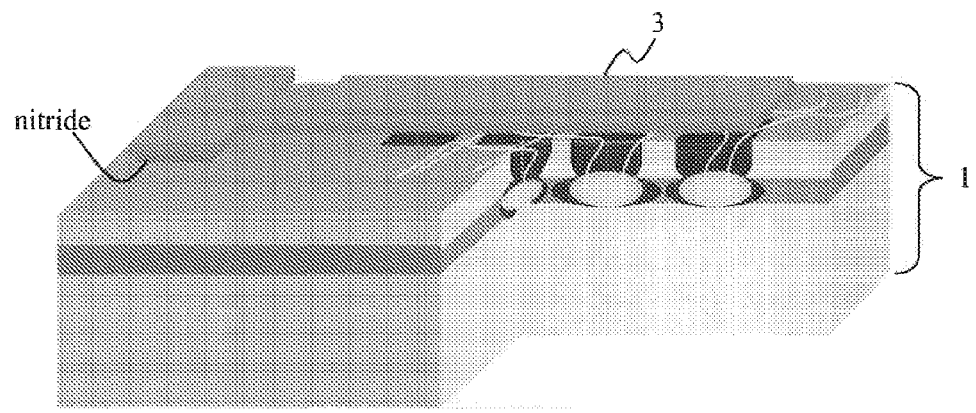

FIGS. 43 to 45 schematically depict how the elongated cantilever fork grating (microactuator) is caused to bend sideways by forcing an electric current through the polysilicon cantilever fork for determining a different thermal elongation by the Joule's heat generated by the current in the two parallel arms of the fork, purposely made with markedly different conductive cross sections.

FIG. 44 shows the introduction through the openings no longer occluded by the microactuator of an embryonal neuronal cell into each cavity. FIG. 45 shows how the cultivated neuronal cells, statically confined in respective cavities, send out processes and neurites passing underneath the overhanging cantilever fork grating that remain spaced about 1 μm from the flat surface of the substrate.

The deflection of the microactuators upon forcing an electric current through them has been determined through finite element analysis using the simulation program ANSYS 6.0. The physical properties of the materials constituting the microacruator system where as reported in the following Tables 1, 2 and 3.

TABLE 1

Physical Properties of the polysilicon

| | |
|---|---|
| Young's modulus | 169 GPa |
| Poisson's coefficient | 0.22 |

TABLE 1-continued

Physical Properties of the polysilicon

| | |
|---|---|
| Resistivity | 2.3 e$^{-11}$ TΩ μm |
| Thermal expansion coefficient | 2.9 e$^{-6}$ 1/K |
| Heat conductivity | 150 e$^{6}$ pW/μmK |
| Density | 2.33 e$^{-15}$ Kg/μm$^{3}$ |

TABLE 2

Physical Properties of silicon nitride

| | |
|---|---|
| Young's modulus | 247.5 GPa |
| Poisson's coefficient | 0.24 |
| Resistivity | 1 e$^{5}$ TΩ μm |
| Thermal expansion coefficient | 3.3 e$^{-6}$ 1/K |
| Heat conductivity | 30 e$^{6}$ pW/μmK |
| Density | 3.1 e$^{-15}$ Kg/μm$^{3}$ |

TABLE 3

Physical Properties of monocrystalline silicon

| | |
|---|---|
| Young's modulus | 165 GPa |
| Poisson's coefficient | 0.22 |
| Resistivity | 2.3 e$^{-11}$ TΩ μm |
| Thermal expansion coefficient | 2.5 e$^{-6}$ 1/K |
| Heat conductivity | 157 e$^{6}$ pW/μmK |
| Density | 2.3 e$^{-15}$ Kg/μm$^{3}$ |

Figure 46:
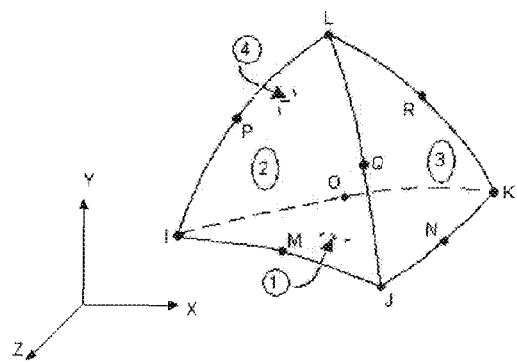
FIGS. 46-57 illustrate the modeling of an overhanging elongated cantilever grating (microactuator) of polysilicon, according to an embodiment of the present invention.
Figure 47:
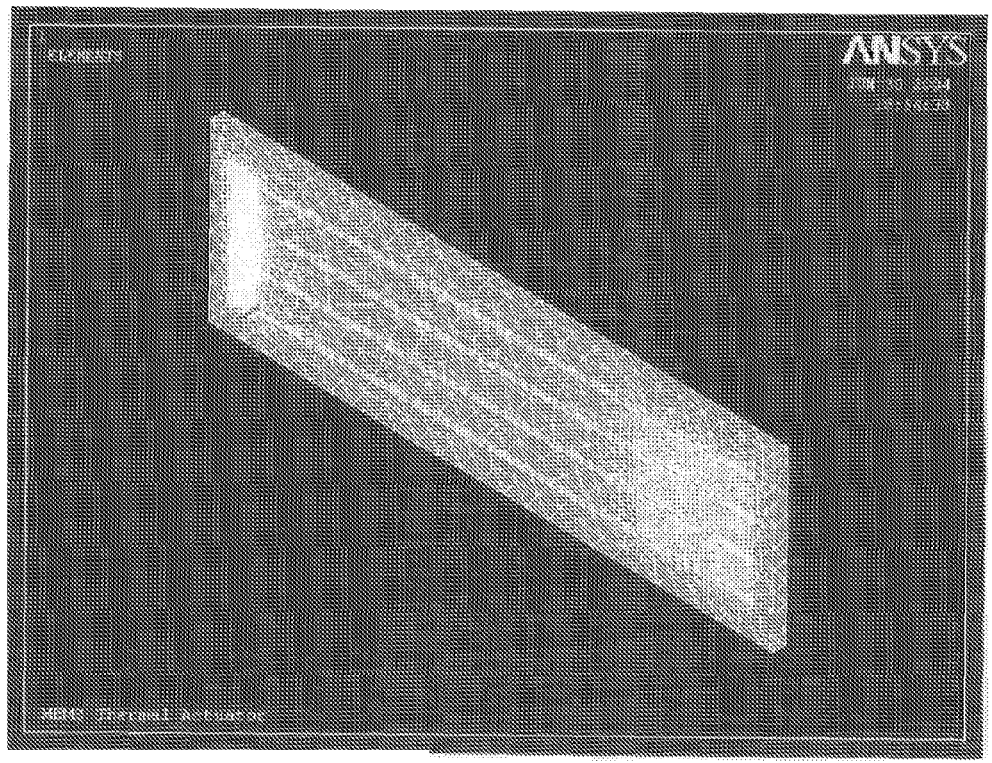

A microactuator 3 formed on a 25 μm thick silicon substrate, for occluding four aligned square openings of 8 μm side length was discretized as a free mash of 82,125 elements as depicted in FIG. 47 (SOLID 98). Geometry, location of nodes and coordinate systems of the elements, are depicted in FIG. 46. Such an element (SOLID 98) of discretization has been selected as particularly suited for carrying our thermal, electrical and structural analysis.

FIGS. 48-57 show the results of the distinct analysis, in particular of the deflection along the cantilevered fork microactuators, the temperature distribution reached in the cantilevered fork microactuator and of the equivalent tensile stress according to Von Mises.

Figure 48:
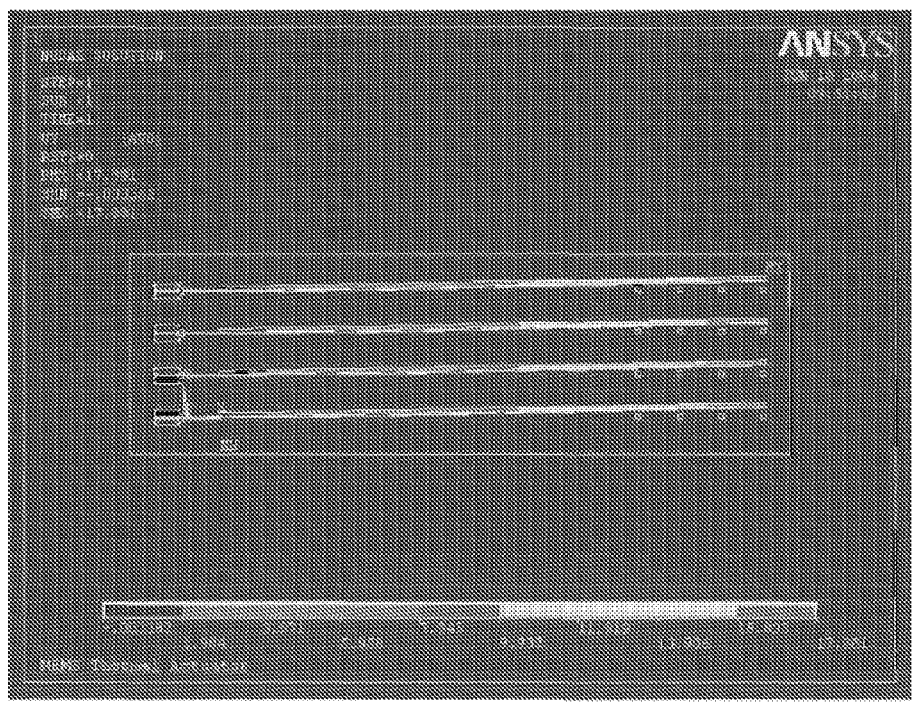
Figure 49:
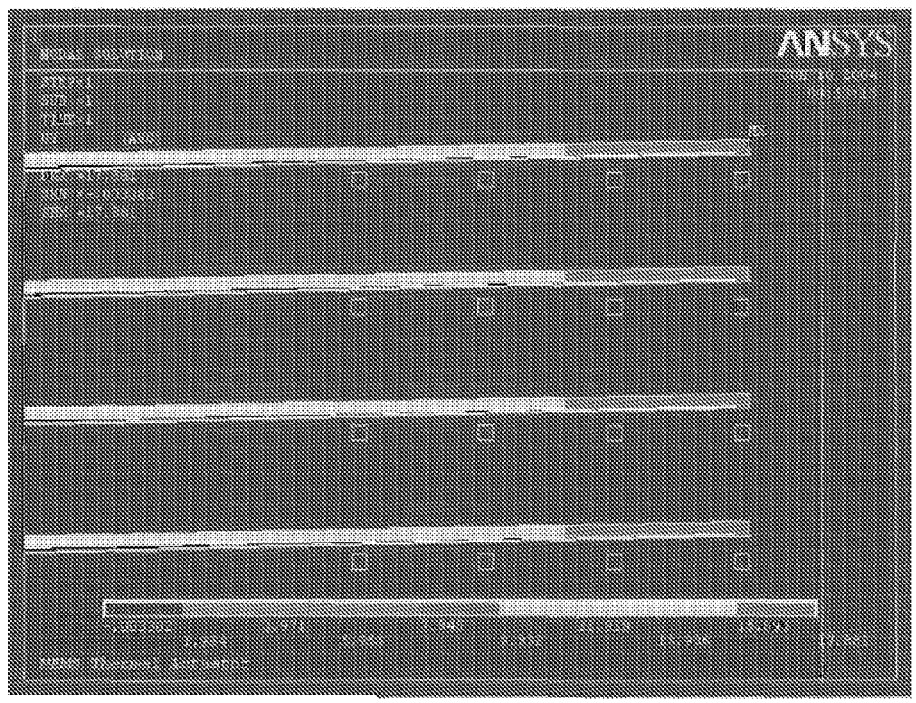

FIGS. 48 and 49 show that the value of deflection in correspondence of each of the four aligned openings that are normally occluded by the microactuator is amply sufficient to permit the introduction of embryonal neuronal cells into the buried cavities.

Figure 50:
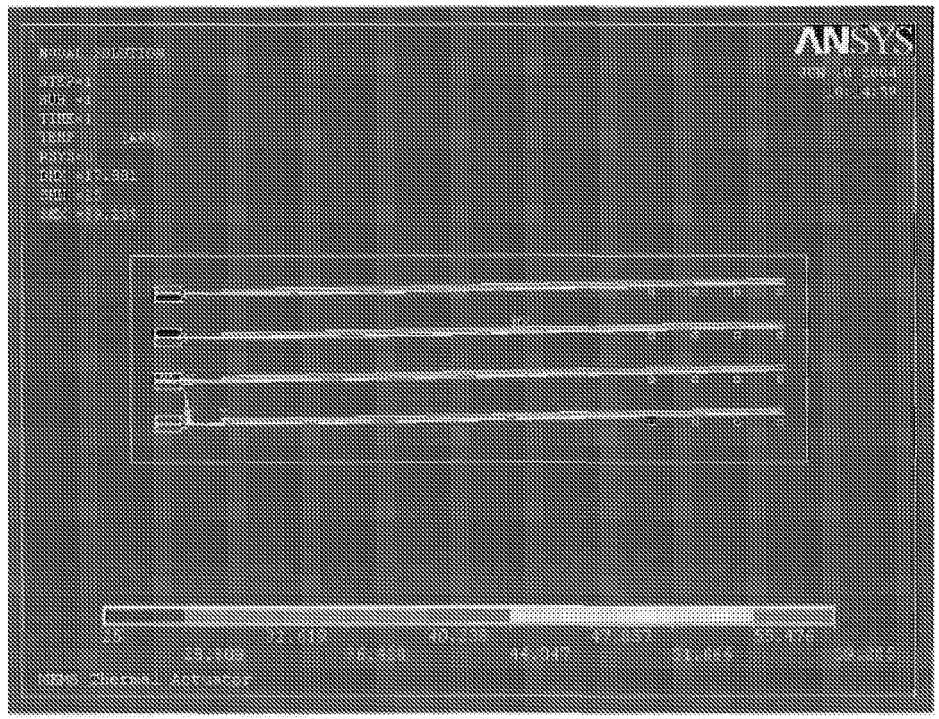
Figure 51:
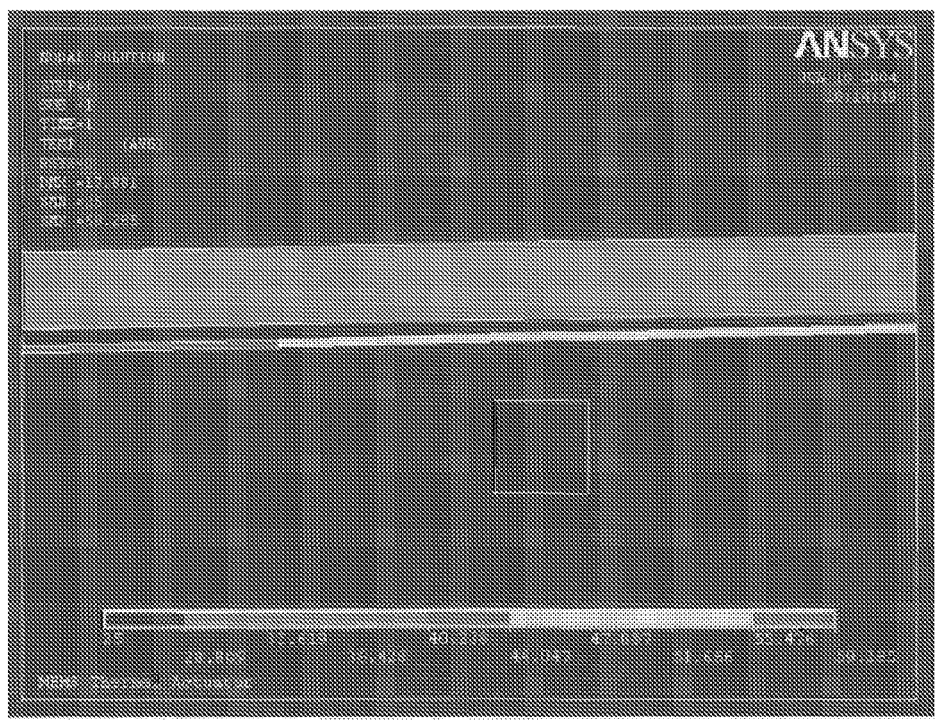
Figure 52:
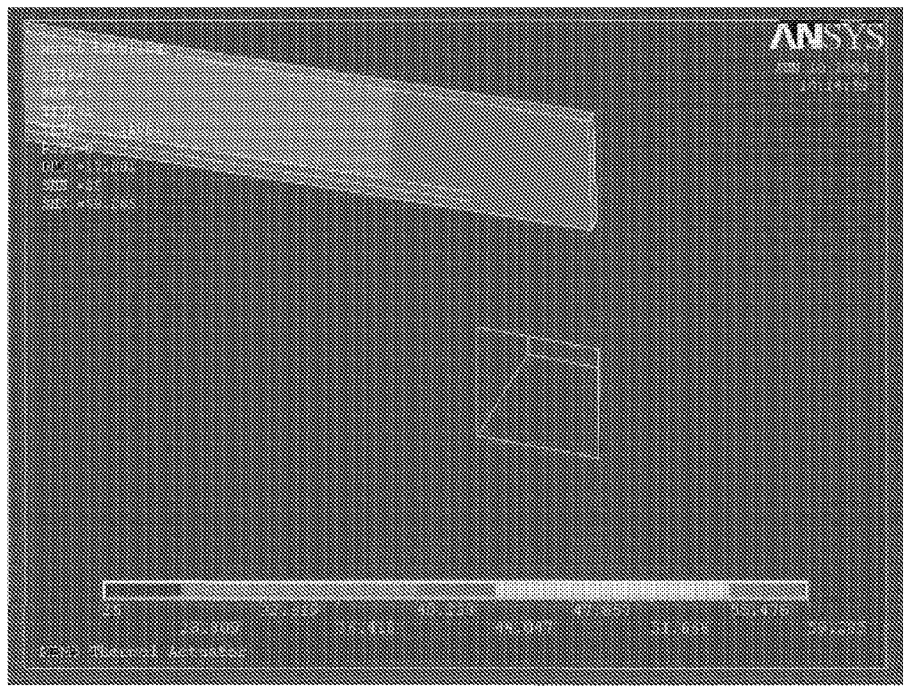

FIGS. 50, 51 and 52 show the temperature distribution reached along the elongated cantilevered fork of polysilicon. As may be recognized, the temperatures reached in the elongated cantilever fork grating remain in a range that is substantially biocompatible for a safe introduction embryonal neuronal cells into the buried cavities. The electrical current that is forced by applying a voltage of 1 Volt to the pads of a microactuator is 0.4790×10$^{7}$ pA and the heat that is generated by Joule's effect along the polysilicon fork microactuator is 0.3538×10$^{7}$ pW.

Figure 53:
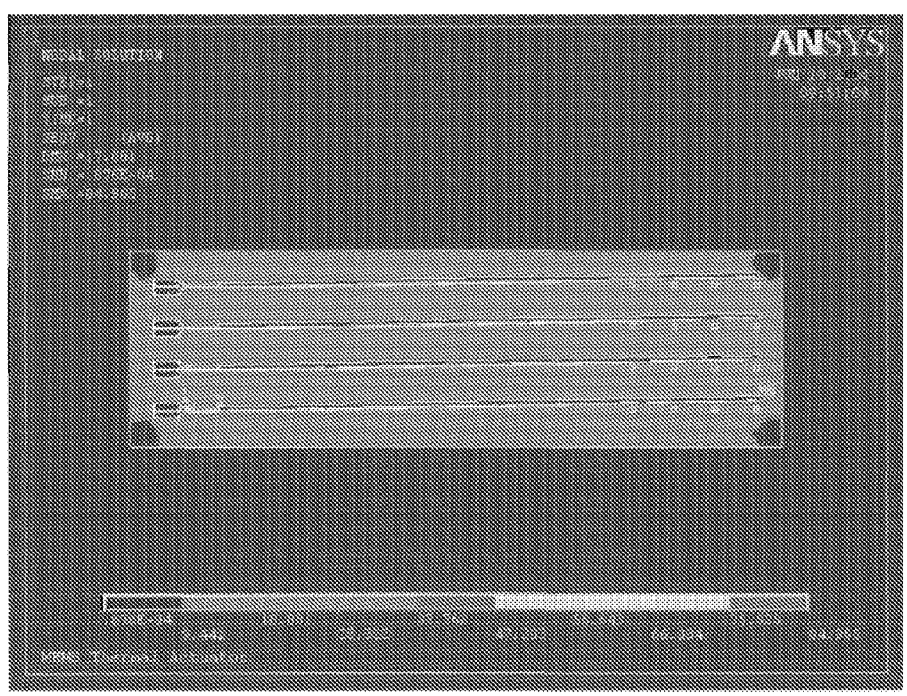

FIG. 53 shows the distribution of the equivalent tensile stress in the whole microactuator structure according to Von Mises; such equivalent tensile stress values represent monodimensional tensile stresses equivalent to the real three-dimensional stress state, in order to determine the yield stress of the structure. The highest value of equivalent tensile stress acting in the microactuator structure occurs in correspondence of the nitride layer that electrically insulates the electrically conductive polysilicon cantilever fork of the microactuator and restrains it by binding it at one end to the surface of the silicon substrate.

Figure 54:
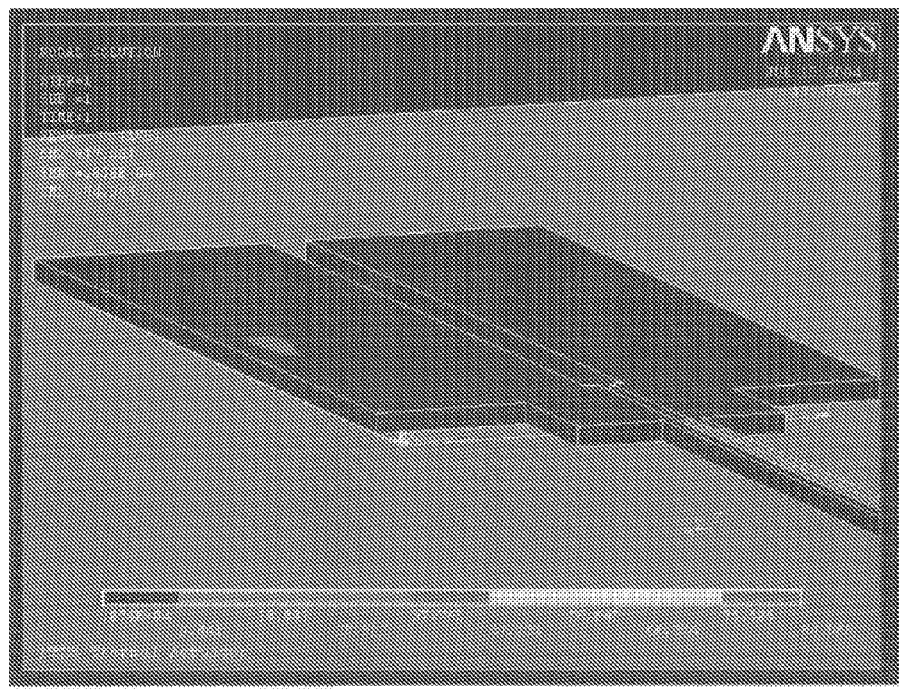

FIG. 54 is an enlarged view of the zone of maximum equivalent tensile stress. In order to verify that the mechanical integrity of the system is never jeopardized, the maximum equivalent tensile stress must be compared to the yield stress of the stressed material(s). The silicon nitride under the polysilicon terminal pads of the two arms of the cantilever fork, is the material that is most stressed and its yield stress is of about 150 MPa. Since the maximum tensile stress found to be acting on the nitride is about 85 MPa, there would appear to be an ample safety margin to ensure the mechanical resistance of the microactuator system.

Along the elongated cantilevered fork portion of the microactuator of polysilicon, the maximum equivalent tensile stress that is reached is 22 MPa and also this value appears to be amply tolerable by the polysilicon with a yield stress of about 500 MPa. The measured maximum equivalent tensile stress in relation to the yield stress of the polysilicon means the mechanical behavior of the microactuator is well within the range defined by Hook's law, that is a linear-elastic behavior.

Figure 55:
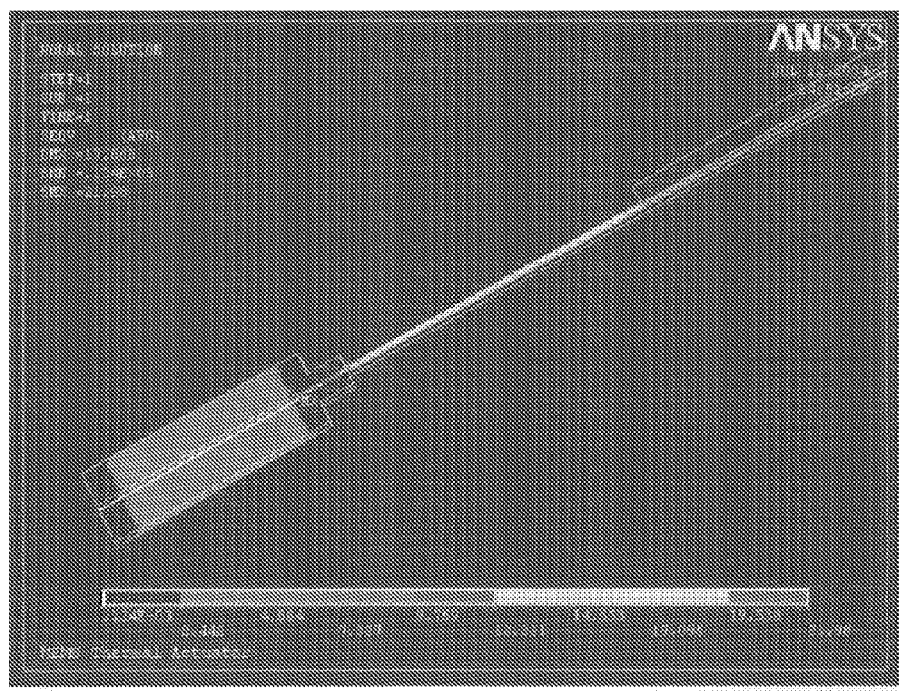
Figure 56:
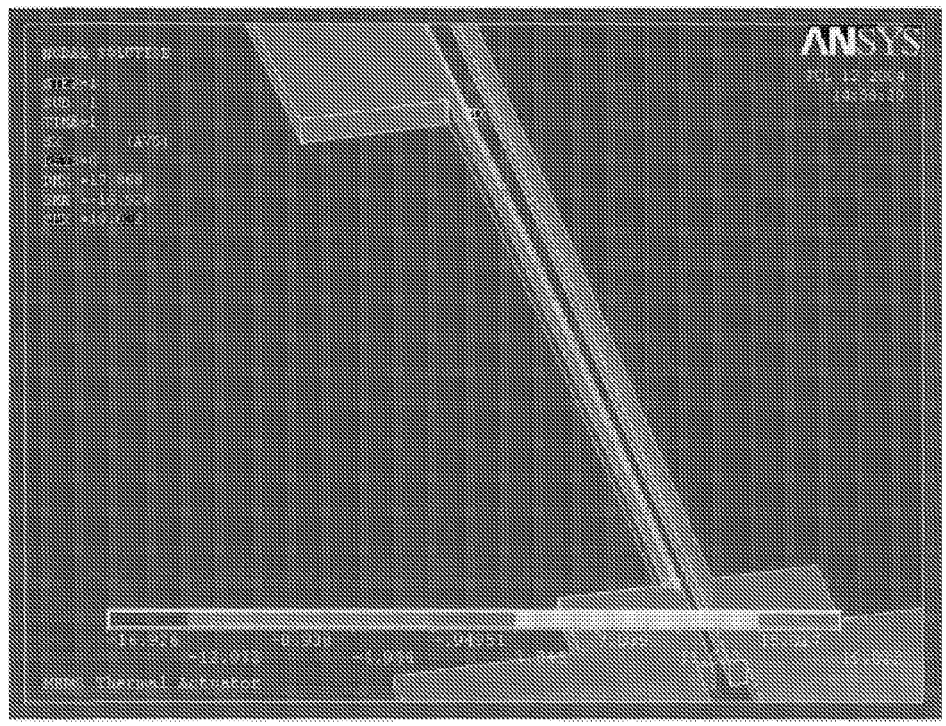
Figure 57:
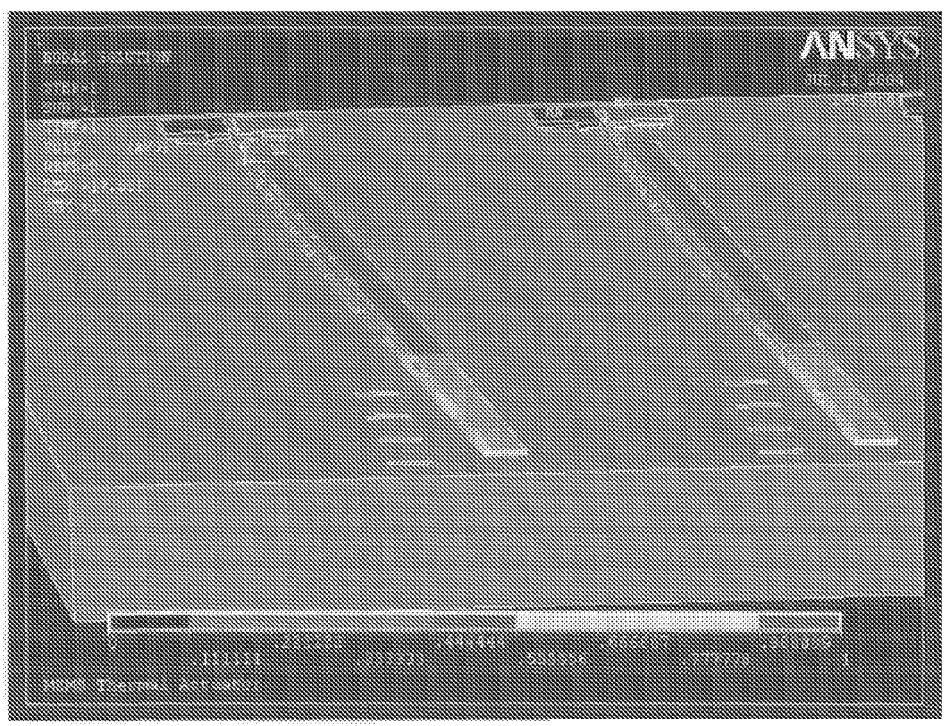

FIGS. 55 and 56 show the distribution of the stresses along the cantilever fork actuator of polysilicon causing substantially rectilinear deflection of the cantilever fork portion freeing the access to the buried cavities. In particular, FIG. 56 shows the typical butterfly distribution of the longitudinal stresses consequent to the deflection of the cantilever microactuator localized in the neck zone in proximity of the anchoring pads of the two arms of the cantilever fork. Finally FIG. 57 shows the voltage distribution along the arms that form the cantilever fork actuator.

Although various embodiments of the method and apparatus of the present invention have been illustrated in the accompanying drawings and described above, it will be understood that the invention is not limited to the embodiments disclosed, but is capable of numerous rearrangements, modifications and substitutions without departing from the spirit of the invention as set forth herein.

The following materials are each incorporated in their entirety by reference.

[1] J. A. Wright, et al., "Towards a Functional MEMS Neurowell by Physiological Experimentation", *Tech. Digest: ASME* 1996 *International Mechanical Engineering Congress and Exposition, DSC-Vol.* 59, Atlanta, Ga., pp. 333-338, November 1996.

[2] www.its.caltech.edu/~pinelab.

[3] G. Zeck, P. Fromherz, "Noninvasive neuroelectronic interfacing with synaptically connected snail neurons immobilized on a semiconductor chip," PNAS, Vol. 98, No. 18, 10457-10462 (2001).

[4] Maher M. P., et al., "The neurochip: a new multielectrode device for stimulating and recording from cultured neurons", J. Neurosci. Methods 1999; 30: 45-56.

The invention claimed is:

1. An improved device for confining cells on a substrate having a well for containing a cell, said well having a well opening, and retention means overhanging said well opening for preventing said cell from leaving said well, wherein said retention means improvement comprises:
   a) a retention grating having at least two coplanar parallel members, wherein said parallel members span said well opening, are of a conductive material, have at least one end electrically accessible and mechanically connected to the substrate, and are elastically deformable sufficient to permit cell access to said well by forcing an electric current through said parallel members.

2. The device of claim 1, wherein both ends of said parallel members are electrically accessible and connected to said substrate and electric current is flowed along said two parallel members in opposite direction, inducing a repulsive force between said two parallel members.

3. The device of claim 2, wherein said two parallel conductive members further comprise:
   a) a bridge portion and two arms of an elongated cantilever fork projecting from two terminal pad portions of relatively large area for electrical connection to a power supply,
   b) said terminal pad portions are mechanically anchored to a surface of said substrate, and
   c) said substrate comprises monocrystalline silicon.

4. The device of claim 3, wherein one of the two parallel arms of said cantilever fork has a cross section area smaller than the cross section area of the other arm of the fork.

5. The device of claim 4, wherein said elongated cantilever fork and said terminal pads comprise polysilicon and said terminal pad portions are electrically insulated and mechanically connected to said substrate by a layer of silicon nitride that spaces the elongated cantilever fork at a distance from the surface of the substrate.

6. The device of claim 5, wherein said distance is about 1 µm.

7. The device of claim 6, where said cell is a neural cell.

8. The device of claim 1, wherein elastic deformation of at least one of said parallel members is accentuated by thermal elongation generated by Joule's effect in said parallel member.

9. The device of claim 1, wherein one of the two parallel members of the retention grating has a cross sectional area smaller than the cross sectional area of the other member.

10. The device of claim 1, wherein said retention grating comprises polysilicon and said substrate comprises monocrystalline silicon.

11. The device of claim 10, wherein retention grating is electrically insulated and mechanically connected to said substrate by a layer of silicon nitride.

12. The device of claim 1, wherein the well opening is substantially square in shape with each side being about 8 µm in length.

13. The device of claim 1, wherein the retention grating extends over a plurality of well openings.

14. A neural network device, comprising:
a) a semiconductor substrate,
b) said substrate having a well for containing a neural cell,
c) said well having a well opening and being electrically coupled to a power source; and
d) a retention grating overhanging said well opening for preventing said neural cell from leaving said well, wherein said retention grating comprises:
   i) at least two coplanar parallel members of a conductive material that span said well opening and at least one end of said parallel members are electrically accessible and mechanically connected to said substrate, and
   ii) said parallel members are elastically deformable sufficient to permit cell access to said well by forcing an electric current through said parallel members.

15. The device of claim 14, wherein said well is electrically coupled to a detector for detecting electrical activity in said cell.

16. The device of claim 14, wherein said well is a buried cavity.

17. The device of claim 14, wherein both ends of said parallel members are electrically accessible and mechanically connected to said substrate and electric current is flowed along said two parallel members in opposite direction to repulse said two parallel members.

18. The device of claim 14, wherein one of the two parallel members has a cross sectional area smaller than the other member and said elastic deformation is accentuated by thermal elongation of said member.

19. The device of claim 14, wherein one of said parallel members is curved to accentuate said elastic deformation.

20. The device of claim 14, wherein said retention grating comprises polysilicon, said substrate comprises monocrystalline silicon, and said retention grating is electrically insulated and mechanically connected to said substrate by a layer of silicon nitride.

21. The device of claim 14, wherein said two parallel conductive members further comprise:
   a) a bridge portion and two arms of an elongated cantilever fork projecting from two terminal pad portions for electrical connection to a power supply,
   b) said terminal pad portions are mechanically anchored to a surface of said substrate, and
   c) said substrate comprises monocrystalline silicon, said elongated cantilever fork comprises polysilicon, said terminal pads comprise polysilicon and are electrically insulated and mechanically connected to said substrate by a layer of silicon nitride.

* * * * *